United States Patent
Haufe et al.

(10) Patent No.: US 10,595,919 B2
(45) Date of Patent: Mar. 24, 2020

(54) SURGICAL TOOLS WITH POSITIONAL COMPONENTS

(71) Applicant: Medovex Corp., Tampa, FL (US)

(72) Inventors: Scott M. W. Haufe, Niceville, FL (US); Robert D. Carter, Apple Valley, MN (US)

(73) Assignee: Medovex Corp., Tampa, FL (US)

( * ) Notice: Subject to any disclaimer, the term of this patent is extended or adjusted under 35 U.S.C. 154(b) by 95 days.

(21) Appl. No.: 15/527,920

(22) PCT Filed: Dec. 10, 2015

(86) PCT No.: PCT/US2015/064988
§ 371 (c)(1),
(2) Date: May 18, 2017

(87) PCT Pub. No.: WO2016/094653
PCT Pub. Date: Jun. 16, 2016

(65) Prior Publication Data
US 2018/0310975 A1    Nov. 1, 2018

Related U.S. Application Data

(60) Provisional application No. 62/093,589, filed on Dec. 18, 2014, provisional application No. 62/091,226, filed on Dec. 12, 2014.

(51) Int. Cl.
*A61B 17/34* (2006.01)
*A61B 17/84* (2006.01)
(Continued)

(52) U.S. Cl.
CPC ...... *A61B 17/8861* (2013.01); *A61B 17/1659* (2013.01); *A61B 17/34* (2013.01);
(Continued)

(58) Field of Classification Search
CPC ..... A61B 17/34; A61B 90/50; A61B 17/3421; A61B 17/3423; A61B 17/3472;
(Continued)

(56) References Cited

U.S. PATENT DOCUMENTS

| 2,001,638 A | 5/1935 | Tornsjo |
| 2,012,362 A | 8/1935 | Vogel |
| (Continued) | | |

FOREIGN PATENT DOCUMENTS

| CN | 2064221 | 10/1990 |
| CN | 101879089 | 11/2010 |
| (Continued) | | |

OTHER PUBLICATIONS

Extended European Search Report corresponding to related European Application No. 15867310.3 (10 pages) (dated May 14, 2018).
(Continued)

*Primary Examiner* — Linda C Dvorak
*Assistant Examiner* — Bradford C. Blaise
(74) *Attorney, Agent, or Firm* — Myers Bigel, P.A.

(57) ABSTRACT

Surgical tools with an upwardly extending tubular support member having a longitudinally extending open channel are provided/described. The tubular support member has a wall surrounding the open channel. The tubular support member may include a base pivotably attached to the tubular support member so that a pivot axis extends above the bottom surface of the base across a bottom portion of the tubular support member to allow the tubular support member to pivot back and forth over a bottom surface of the base. The tubular support member can cooperate with downwardly extending k-wires that anchor to patient bone and/or a strap. One or all of the base, strap and/or k-wires may be used with surgical tools for treating back pain use a spinal facet debridement tool with cautery and denuding action and minimally invasive protocol that can denude and cauterize soft tissue associated with a synovial capsule of the spinal facet joint.

26 Claims, 24 Drawing Sheets

(51) Int. Cl.

| | | |
|---|---|---|
| *A61B 90/50* | (2016.01) | |
| *A61B 18/00* | (2006.01) | |
| *A61B 17/00* | (2006.01) | |
| *A61B 17/88* | (2006.01) | |
| *A61B 18/14* | (2006.01) | |
| *A61B 17/16* | (2006.01) | |
| *A61B 17/90* | (2006.01) | |

(52) U.S. Cl.
CPC ...... *A61B 17/3421* (2013.01); *A61B 17/3472* (2013.01); *A61B 17/848* (2013.01); *A61B 18/14* (2013.01); *A61B 18/148* (2013.01); *A61B 90/50* (2016.02); *A61B 17/3423* (2013.01); *A61B 2017/00398* (2013.01); *A61B 2017/347* (2013.01); *A61B 2017/3407* (2013.01); *A61B 2017/3443* (2013.01); *A61B 2017/3492* (2013.01); *A61B 2017/90* (2013.01); *A61B 2018/00208* (2013.01); *A61B 2018/00339* (2013.01); *A61B 2018/00595* (2013.01); *A61B 2217/005* (2013.01)

(58) Field of Classification Search
CPC .......... A61B 2017/3407; A61B 17/848; A61B 2017/3443; A61B 2017/347; A61B 2017/3492; A61B 17/8861; A61B 2017/90
See application file for complete search history.

(56) References Cited

U.S. PATENT DOCUMENTS

| | | | |
|---|---|---|---|
| 4,002,169 A | 1/1977 | Cupler, II | |
| 4,314,568 A | 2/1982 | Loving | |
| 4,658,819 A | 4/1987 | Harris et al. | |
| 4,813,939 A * | 3/1989 | Marcus | A61M 39/0208 604/174 |
| 4,969,885 A | 11/1990 | Farin | |
| 4,983,179 A | 1/1991 | Sjostrom | |
| 4,991,578 A | 2/1991 | Cohen | |
| 5,312,332 A | 5/1994 | Bales et al. | |
| 5,364,395 A | 11/1994 | West, Jr. | |
| 5,545,195 A | 8/1996 | Lennox et al. | |
| 5,569,290 A | 10/1996 | McAfee | |
| 5,573,533 A | 11/1996 | Strul | |
| 5,584,843 A | 12/1996 | Wulfman et al. | |
| 5,618,296 A | 4/1997 | Sorensen et al. | |
| 5,633,578 A | 5/1997 | Eggers et al. | |
| 5,693,045 A | 12/1997 | Eggers | |
| 5,807,395 A | 9/1998 | Mulier et al. | |
| 5,819,734 A | 10/1998 | Deily et al. | |
| 5,849,023 A | 12/1998 | Mericle | |
| 5,855,576 A | 1/1999 | LeVeen et al. | |
| 5,865,810 A | 2/1999 | Perry et al. | |
| 5,904,681 A | 5/1999 | West, Jr. | |
| 5,941,876 A | 8/1999 | Nardella et al. | |
| 5,957,863 A | 9/1999 | Koblish et al. | |
| 6,007,533 A | 12/1999 | Casscells et al. | |
| 6,032,673 A | 3/2000 | Savage et al. | |
| 6,142,992 A | 11/2000 | Cheng et al. | |
| 6,214,001 B1 | 4/2001 | Casscells et al. | |
| 6,406,424 B1 | 6/2002 | Williamson, IV et al. | |
| 6,416,490 B1 | 7/2002 | Ellis et al. | |
| 6,454,764 B1 | 9/2002 | Fleenor et al. | |
| 6,524,238 B2 | 2/2003 | Velikaris et al. | |
| 6,579,281 B2 | 6/2003 | Palmer et al. | |
| 6,610,059 B1 | 8/2003 | West, Jr. | |
| 6,663,628 B2 | 12/2003 | Peters | |
| 6,770,070 B1 | 8/2004 | Balbierz | |
| 6,797,332 B2 | 9/2004 | Strangman et al. | |
| 6,827,725 B2 | 12/2004 | Batchelor et al. | |
| 7,001,333 B2 | 2/2006 | Hamel et al. | |
| 7,052,494 B2 | 5/2006 | Goble et al. | |
| 7,150,747 B1 | 12/2006 | McDonald et al. | |
| 7,326,177 B2 | 2/2008 | Williamson, IV et al. | |
| 7,331,956 B2 | 2/2008 | Hovda et al. | |
| 7,361,174 B2 | 4/2008 | Bee et al. | |
| 7,674,263 B2 | 3/2010 | Ryan | |
| 7,736,361 B2 | 6/2010 | Palanker et al. | |
| 7,789,879 B2 | 9/2010 | Palanker et al. | |
| 7,942,874 B2 | 5/2011 | Eder et al. | |
| 8,012,153 B2 | 9/2011 | Woloszko et al. | |
| 8,043,286 B2 | 10/2011 | Palanker et al. | |
| 8,167,879 B2 | 5/2012 | Haufe | |
| 8,323,276 B2 | 12/2012 | Palanker et al. | |
| 8,343,189 B2 | 1/2013 | Assell et al. | |
| 8,394,129 B2 | 3/2013 | Lopez et al. | |
| 8,500,727 B2 | 8/2013 | Aramayo | |
| 2001/0000531 A1 | 4/2001 | Casscells et al. | |
| 2002/0165549 A1 | 11/2002 | Owusu-Akyaw et al. | |
| 2003/0153926 A1 | 8/2003 | Schmieding et al. | |
| 2003/0195392 A1 | 10/2003 | Hamel et al. | |
| 2004/0030330 A1 | 2/2004 | Brassell et al. | |
| 2004/0078037 A1 | 4/2004 | Batchelor et al. | |
| 2005/0070765 A1 | 3/2005 | Abdelgany et al. | |
| 2005/0245923 A1 | 11/2005 | Christopherson et al. | |
| 2006/0058780 A1 | 3/2006 | Edwards et al. | |
| 2006/0094976 A1 | 5/2006 | Bleich | |
| 2006/0095059 A1 | 5/2006 | Bleich et al. | |
| 2006/0100501 A1 * | 5/2006 | Berkelman | A61B 17/3403 600/415 |
| 2006/0178670 A1 | 8/2006 | Woloszko et al. | |
| 2007/0049920 A1 | 3/2007 | McClurken et al. | |
| 2007/0129719 A1 | 6/2007 | Kendale et al. | |
| 2007/0293724 A1 | 12/2007 | Saadate et al. | |
| 2008/0015565 A1 | 1/2008 | Davison | |
| 2008/0161670 A1 | 7/2008 | King et al. | |
| 2008/0163870 A1 | 7/2008 | Kusunoki et al. | |
| 2008/0188848 A1 | 8/2008 | Deutmeyer et al. | |
| 2008/0249553 A1 | 10/2008 | Gruber et al. | |
| 2009/0012362 A1 * | 1/2009 | Kucklick | A61B 1/317 600/121 |
| 2010/0010449 A1 | 1/2010 | Leibowitz et al. | |
| 2010/0145142 A1 | 6/2010 | Begemann et al. | |
| 2011/0087217 A1 | 4/2011 | Yates et al. | |
| 2012/0179070 A1 | 7/2012 | Pommer et al. | |
| 2013/0190809 A1 * | 7/2013 | Vidlund | A61B 17/0057 606/213 |
| 2013/0289399 A1 * | 10/2013 | Choi | A61B 17/1671 600/431 |
| 2014/0046380 A1 * | 2/2014 | Asfora | A61B 17/1615 606/304 |
| 2014/0066750 A1 * | 3/2014 | Piferi | A61B 90/11 600/417 |
| 2014/0100567 A1 | 4/2014 | Edwards | |
| 2014/0324044 A1 | 10/2014 | Haufe et al. | |
| 2015/0366548 A1 * | 12/2015 | Lauchner | A61B 17/3423 600/206 |
| 2016/0007979 A1 * | 1/2016 | Bhagat | A61B 17/3403 604/175 |
| 2016/0015891 A1 * | 1/2016 | Papiorek | A61M 5/158 604/180 |
| 2016/0030106 A1 | 2/2016 | Carter et al. | |
| 2016/0213415 A1 | 7/2016 | Carter et al. | |
| 2016/0367331 A1 * | 12/2016 | Nelson | A61B 90/11 |
| 2017/0086813 A1 * | 3/2017 | Hess | A61B 17/0218 |
| 2017/0135721 A1 * | 5/2017 | Pacak | A61B 17/34 |
| 2017/0196590 A1 * | 7/2017 | Sperry | A61B 17/3403 |
| 2018/0008367 A1 * | 1/2018 | Rau | A61B 90/11 |
| 2018/0338812 A1 * | 11/2018 | Morey | A61B 34/20 |
| 2019/0307937 A1 * | 10/2019 | Fitzgerald | A61B 17/3421 |

FOREIGN PATENT DOCUMENTS

| | | |
|---|---|---|
| CN | 102641152 | 8/2012 |
| CN | 202637105 | 1/2013 |
| WO | WO 97/33523 A1 | 9/1997 |
| WO | WO 2005/058132 A2 | 6/2005 |

(56) References Cited

FOREIGN PATENT DOCUMENTS

WO   WO 2008/060277 A2   5/2008
WO   WO 2014/176141      10/2014

OTHER PUBLICATIONS

International Preliminary Report on Patentability corresponding to International Patent Application No. PCT/US2015/064988 (13 pages) (dated Jun. 13, 2017).
International Search Report and the Written Opinion of the International Searching Authority corresponding to International Patent Application No. PCT/US2015/064988 (16 pages) (dated Apr. 19, 2016).

* cited by examiner

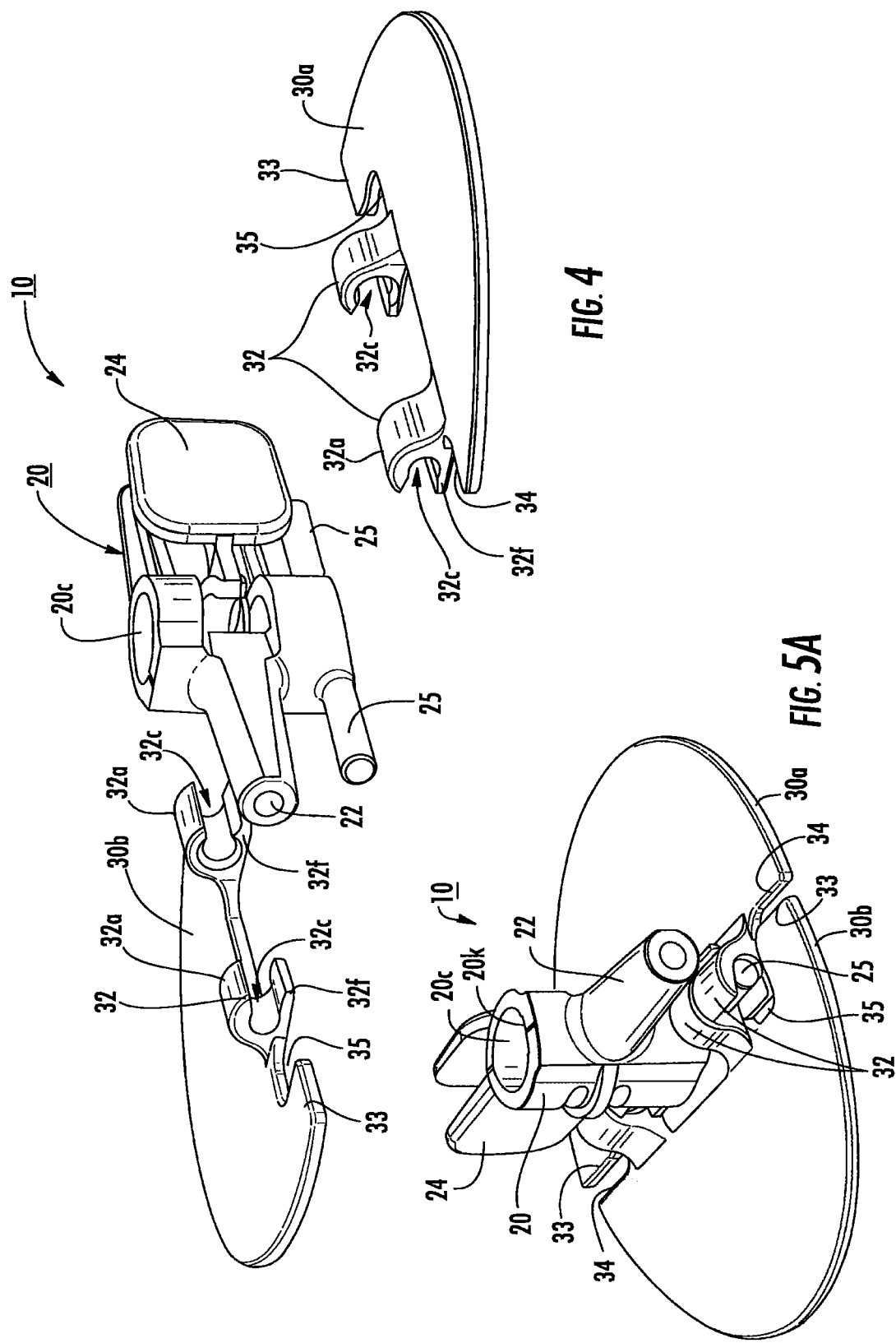

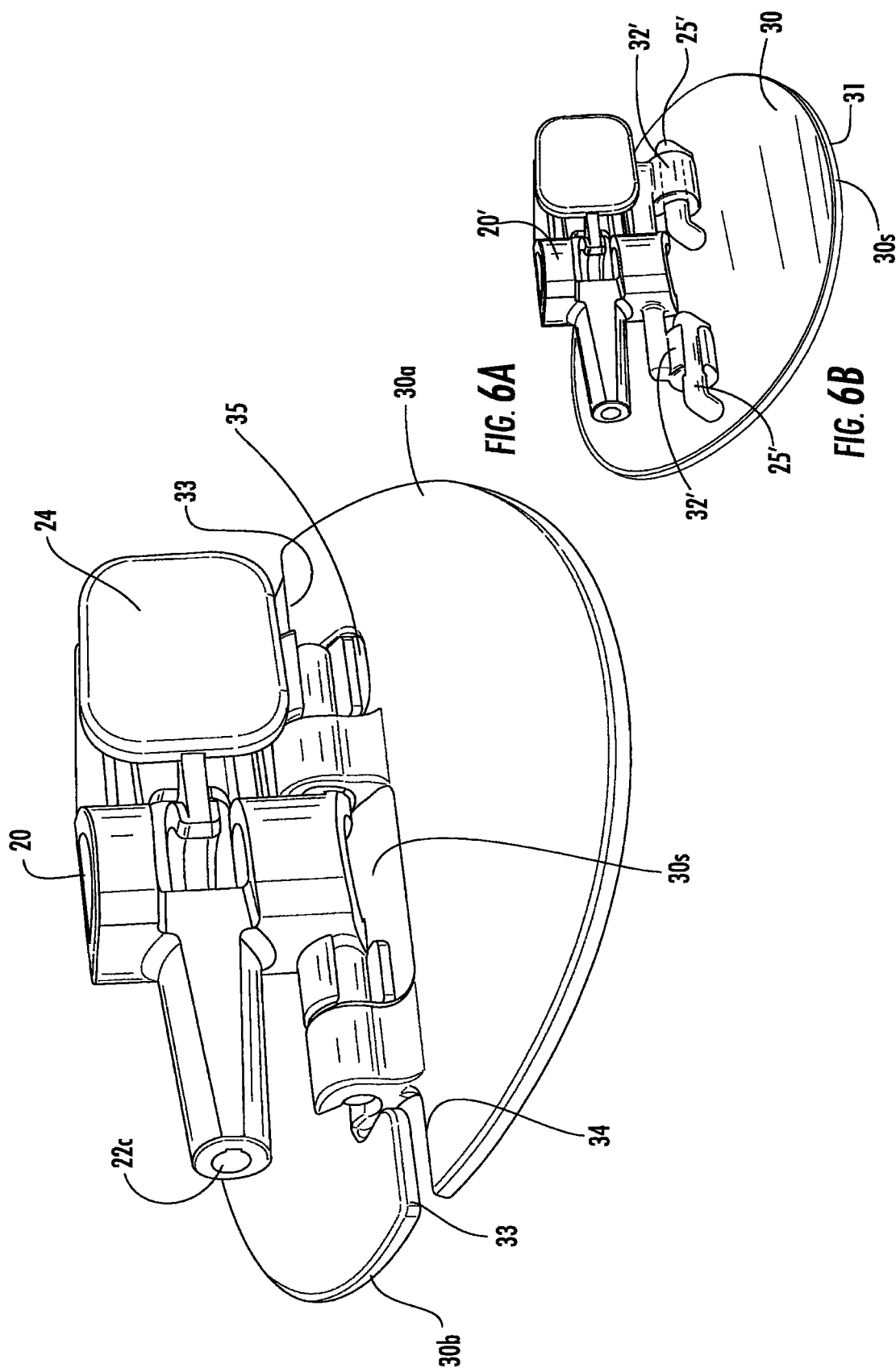

SURGICAL TOOLS WITH POSITIONAL COMPONENTS

RELATED APPLICATIONS

This application claims the benefit of and priority to U.S. Provisional Application Ser. No. 62/091,226 filed Dec. 12, 2014 and U.S. Provisional Application Ser. No. 62/093,589 filed Dec. 18, 2014, the contents of which are hereby incorporated by reference as if recited in full herein.

FIELD OF THE INVENTION

The present invention relates to surgical tools that may be particularly suitable for spinal medical procedures.

BACKGROUND

Some surgical procedures insert surgical tools into the body via tubes or portals to carry out minimally invasive procedures. It may be desirable to provide external support or stabilizers for some procedures. When placing such a support against skin or soft tissue, it can be difficult to accommodate different size/locations of different patients while providing a sufficiently stable device-tissue interface contact surface.

SUMMARY OF EMBODIMENTS OF THE INVENTION

Embodiments of the invention are directed to surgical tools with an upwardly extending tubular member having a longitudinally extending open channel are provided/described. The tubular member has a wall surrounding the open channel. The tubular member may include a base pivotably attached to the tubular support member so that a pivot axis extends above the bottom surface of the base across a bottom portion of the tubular support member to allow the tubular support member to pivot back and forth over a bottom surface of the base. The tubular member can cooperate with downwardly extending k-wires that anchor to patient bone and/or a strap. The base, strap and/or k-wires may be used with surgical tools for treating back pain use a spinal facet debridement tool with cautery and denuding action and minimally invasive protocol that can denude and cauterize soft tissue associated with a synovial capsule of the spinal facet joint.

Embodiments of the present invention provide stabilizers that can be configured with a base that resides against skin and/or soft tissue of a patient and that can support a tube guide in a manner that allows the tube guide to articulate and/or pivot relative to the stabilizer.

Embodiments of the present invention can employ the stabilizer with a surgical tool that can be used to provide relatively rapid, minimally invasive and cost effective treatments for long term, typically permanent, pain relief for spinal arthritis and/or spinal facet arthritis pain.

Embodiments of the invention are directed to surgical tools that include an upwardly extending tubular member having a longitudinally extending open channel. The tubular member has a wall surrounding the open channel and at least one of the following: (a) a base pivotably attached to the tubular support member so that a pivot axis extends above the bottom surface of the base across a bottom portion of the tubular support member to allow the tubular support member to pivot back and forth over a bottom surface of the base; (b) a plurality of circumferentially spaced apart k-wires held by the tubular member; and/or (c) at least one strap attached to the tubular member.

Embodiments of the present invention provide a stabilizer that may have the base of (a) and the base may have two opposed segments that can independently articulate, one on opposing sides of a tubular support held by the base.

The surgical tools can include the k-wires of configuration (b) and the tubular member can include longitudinally extending channels that receive a respective k-wire.

The surgical tools can have the strap of configuration (c) and the strap can attach to an anchor pad under a patient or have a length sufficient to define a closed configuration extending about a torso of a patient.

Embodiments of the invention are directed to surgical tools that include an upwardly extending tubular member having a longitudinally extending open channel. The tubular support member also has a wall surrounding the open channel.

The tools may further include a base pivotably attached to the tubular member so that a pivot axis extends above the bottom surface of the base across a bottom portion of the tubular support member to allow the tubular support member to pivot back and forth over a bottom surface of the base.

The tools can have one or more of the following: (a) a base pivotably attached to the tubular support member having a pivot axis that extends above a bottom surface of the base across a bottom portion of the tubular member; (b) a plurality of circumferentially spaced apart k-wires held by the tubular support member; and/or (c) at least one strap attached to the tubular support member.

For the configuration comprising (a), the tubular member can include an open longitudinally extending channel that holds the guide cannula with the shaft of the debrider tool extending through the guide cannula to allow the tubular member, guide cannula and rotatable shaft to pivot back and forth about the pivot axis over the bottom surface of the base while the shaft of the tool rotates during a therapy.

The pivot axis can extend through an axially extending centerline of first and second laterally spaced apart attachment members held by one of the tubular support member or base that cooperate with hinge members held by the other of the tubular support member or base to allow the tubular support member to pivot above the bottom surface of the base as the laterally extending arms rotate in the hinge members.

The tubular support member can include spaced apart first and second laterally outwardly extending base attachment members that define a pivot axis. The base can include a plurality of hinge members, at least one that engages the first base attachment member and at least one that engages the second base attachment member whereby the tubular support member can pivot relative to the base.

The laterally extending base attachment members can be cylindrical.

The base can include first and second base members (optionally with planar bottom surfaces), one attached to each side of the tubular support member, each configured to move independent of the other.

The bottom surface of the base can be curved in a direction facing away from the tube.

The bottom surface of the base can have a radius of curvature that is between about 4 inches to about 12 inches.

The base can have a unitary member with upwardly extending hinge members that engage laterally outwardly extending arms extending off the wall of the tubular support member. The bottom surface can be sized and configured to reside against skin of a patient and has a width and/or length that is between about 2-6 inches.

The tubular support member can include at least one elongate outwardly extending fluid channel in fluid communication with the longitudinally extending open channel.

The base can have a planar bottom surface and the bottom surface of the base can have a width that is between about 2-6 inches.

The tubular support member can include first and second laterally extending attachment arms extending outwardly off the wall of the tubular support member that define the pivot axis. The base can include first and second base members, each having upwardly extending first and second spaced apart hinge members. One of which can be attached to the first attachment arm and another of which can be attached to the second attachment arm so that the first and second base members can move up and down independent of the other and the tubular support member can pivot relative to the base.

The tubular support member can include laterally outwardly extending finger grips.

The surgical tool can be used with a guide cannula sized and configured to be held in the open channel of the tubular support member.

The tubular support member can include at least one elongate outwardly extending fluid channel in fluid communication with the longitudinally extending open channel thereof. The guide cannula can have a wall that surrounds an open longitudinally extending channel. The wall can include at least one laterally extending open aperture in fluid communication with the fluid channel of the tubular support member.

The first and second base members can be substantially semi-circular and can be held by the tubular support member to form a circular base member.

The pivot axis can extend through an axially extending centerline of first and second laterally spaced apart attachment arms held by one of the tubular support member or base that cooperate with hinge members held by the other of the tubular support member or base to allow the tubular support member to pivot above the bottom surface of the base as the laterally extending attachment arms rotate in the hinge members. The attachment arms can be cylindrical and the hinge members can define a laterally extending cylindrical channel that slidably engage the cylindrical attachment arms.

The hinge members can have an arcuate upper segment and merge into a flat bottom segment under the cylindrical channel.

The surgical tool can be used in combination with a debridement surgical tool that extends through the open channel of the guide cannula while the guide cannula is held by the tubular support member.

Embodiments of the invention are directed to surgical tools for spinal facet therapies. The tools can include: (a) a debrider tool with an elongate rotatable shaft having a distal end with a denuding and cauterization head, and a motor in communication with the shaft to drive the rotatable denuding and cauterization head; (b) a guide cannula that holds the shaft of the debrider tool during a therapy; and (c) an external stabilizer sized and configured to reside against skin of a patient and control an insertion depth of the distal end of the rotatable shaft. The external stabilizer can include a base and a tubular support member pivotably attached to the base so that a pivot axis extends above a bottom surface of the base across a bottom portion of the tubular support member. The tubular support member can include an open longitudinally extending channel that holds the guide cannula with the shaft of the debrider tool extending through the guide cannula to allow the tubular support member, guide cannula and rotatable shaft to pivot back and forth about the pivot axis over the bottom surface of the base while the shaft of the tool rotates during a therapy.

The base comprises first and second base members, one attached to each side of the tubular support member, each configured to move independent of the other.

The pivot axis of the stabilizer can extend through an axially extending centerline of first and second laterally spaced apart attachment members held by one of the tubular support member or base that cooperate with hinge members held by the other of the tubular support member or base to allow the tubular support member to pivot above the bottom surface of the base as the laterally extending arms rotate in the hinge members.

The external stabilizer can include at least one fluid channel extending laterally outwardly from a wall of the tubular support member, wherein the at least one fluid channel is in fluid communication with an open longitudinally extending channel of the guide cannula.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Other systems and/or methods according to embodiments of the invention will be or become apparent to one with skill in the art upon review of the following drawings and detailed description. It is intended that all such additional systems, methods, and/or devices be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings.

FIG. 4 is an exploded view of the stabilizer according to embodiments of the present invention.

FIG. 5A is an enlarged side perspective view of the stabilizer shown in FIGS. 1A and 1B according to embodiments of the present invention.

FIG. 6A is a side perspective view of the stabilizer shown in FIG. 5A.

FIG. 6B is a schematic illustration of an alternate embodiment of the stabilizer, according to embodiments of the present invention.

DETAILED DESCRIPTION OF EMBODIMENTS OF THE INVENTION

Figure 1A:
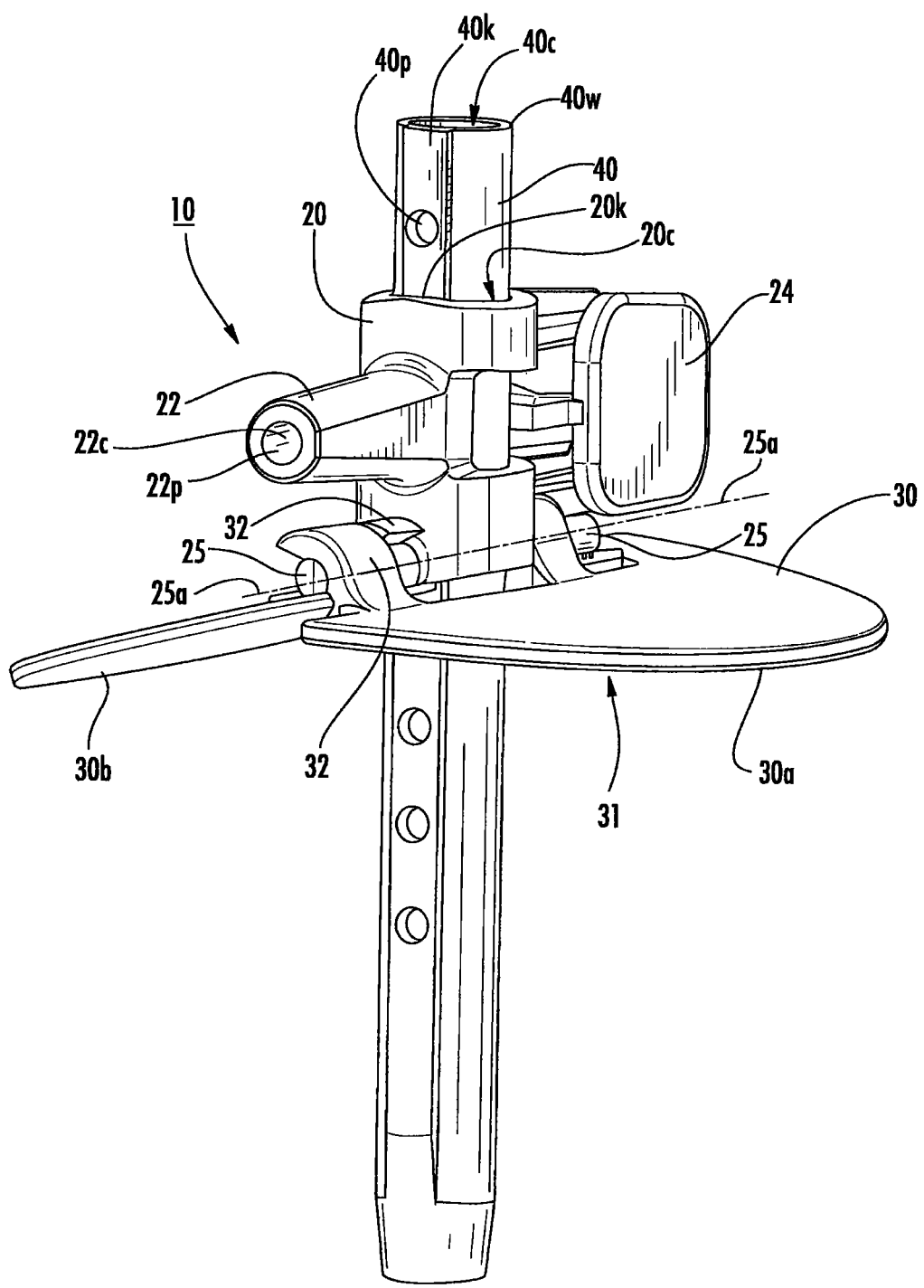
FIG. 1A is a side perspective view of a guide cannula held by a cooperating stabilizer according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. One or more features shown and discussed with respect to one embodiment may be included in another embodiment even if not explicitly described or shown with another embodiment. The term "Fig." (whether in all capital letters or not) is used interchangeably with the word "Figure" as an abbreviation thereof in the specification and drawings. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise. In the claims, the word "a" with respect to an element is intended to include one or more of such elements and is not limited to a single such element unless stated otherwise.

The term "about" means that the recited number or value can vary by +/−20%.

The term "sterile" means that the noted device or material meets or exceeds defined medical guidelines of cleanliness as is well known to those of skill in the art to be substantially (if not totally) without contaminants so as to be suitable for medical uses and/or comply with defined medical guidelines, rules and/or regulations.

Embodiments of the invention are suitable for human or animal use, and are particularly suitable for human use.

The term "fluted" and derivatives thereof refer to recesses, typically flat or concave grooves, on one or more of the inner wall, outer wall, or shaft of a barrel, drive shaft, rotatable head or column of a surgical tool.

The term "denudement" and derivatives thereof refer to a procedure to polish, (gently) grind, scrape, file, grate, cleanse and/or rasp away soft tissue of facet joints to thereby denude tissue and uncover or expose the underlying bone without cutting into or removing the bone (e.g., in contrast to a sharp cutting edge like a knife). The denudement tool can have a surface that has an abrasive texture and/or configuration which may include small teeth.

The term "debridement" and derivatives thereof refer to the removal of soft tissue associated with an end plate receptor region of a target spinal facet joint including the synovial capsule and tissue scraping of an outer boney surface of the joint.

Referring now to the figures, FIGS. 1A-6A illustrate an example of a surgical tool with a tubular support member 20 with a cooperating external base 30. The tool can be described as a stabilizer 10. That is, in some embodiments, the stabilizer tool can include a base 30 that can reside against skin S of a patient (FIG. 10), typically external of the patient body. The bottom surface 31 of the base 30 can be configured to directly abut the skin S of the patient. In other embodiments, a sterile film can reside between the base and the skin (not shown). The bottom surface 31 can be textured or smooth. The bottom 31 may comprise an adhesive or double sided sticky tape or be adhesive-free or tape free.

The base 30 can have a larger perimeter and cross-sectional and/or surface area than the tubular support member 20. The lower surface 31 of the base 30 can be configured to contact skin S on each side of the tubular support member 20. The base 30 can be configured to flex against the skin S of the patient and/or be able to engage skin S over a target entry site entirely about the perimeter of the tubular support member 20, typically so that the base lower surface 31 engages tissue for at least 75% of the surface area of the base lower surface 31.

As shown in FIG. 1A, the base 30 and tubular support member 20 can be attached to each other in a manner that allows one or both of the tubular support member 20 and the base 30 to move relative to each another.

As shown in FIGS. 1A-6A, for example, the tubular support member 20 can include first and second laterally extending, base attachment arms 25, one on each side of the longitudinally extending channel 20c. As shown, the base attachment arms 25 are cylindrical and are configured in an orientation that is orthogonal to the longitudinally extending through channel 20c of the tubular support member 20. The arms 25 may have other shapes, e.g., may be semi-circular or have a body with an upper arcuate portion or otherwise configured to attach to the base.

The laterally extending arms 25 can be in-line with each other across (separated by) the open through channel 20c. The base 30 can include hinge members 32 that attach to the arms 25. The base attachment arms 25 can have an axially extending center line 25a (FIG. 2) that extends through the cylindrical arms 25 and the center channel 20c of the tubular support member 20 and define a hinge axis that resides above the bottom of the base 31.

As shown in FIG. 6B, for example, it is contemplated that the base 30 can be configured with laterally extending arms 25 and the tubular support member 20 can have the hinge members 32 that would allow the base 30 and tubular support member 20 to move relative to each other.

The tubular support member 20 can pivot back and forth relative to the base 30 as the laterally extending arms 25 rotate in the hinge members 32. This allows the guide cannula 40 (FIGS. 1A, 1B, 2) to rotate and/or pivot side to side about the hinge axis 25a, along with any surgical tool extending through the support member 20 and/or guide cannula 40, when the base 30 is held against skin S of the patient.

Figure 1B:
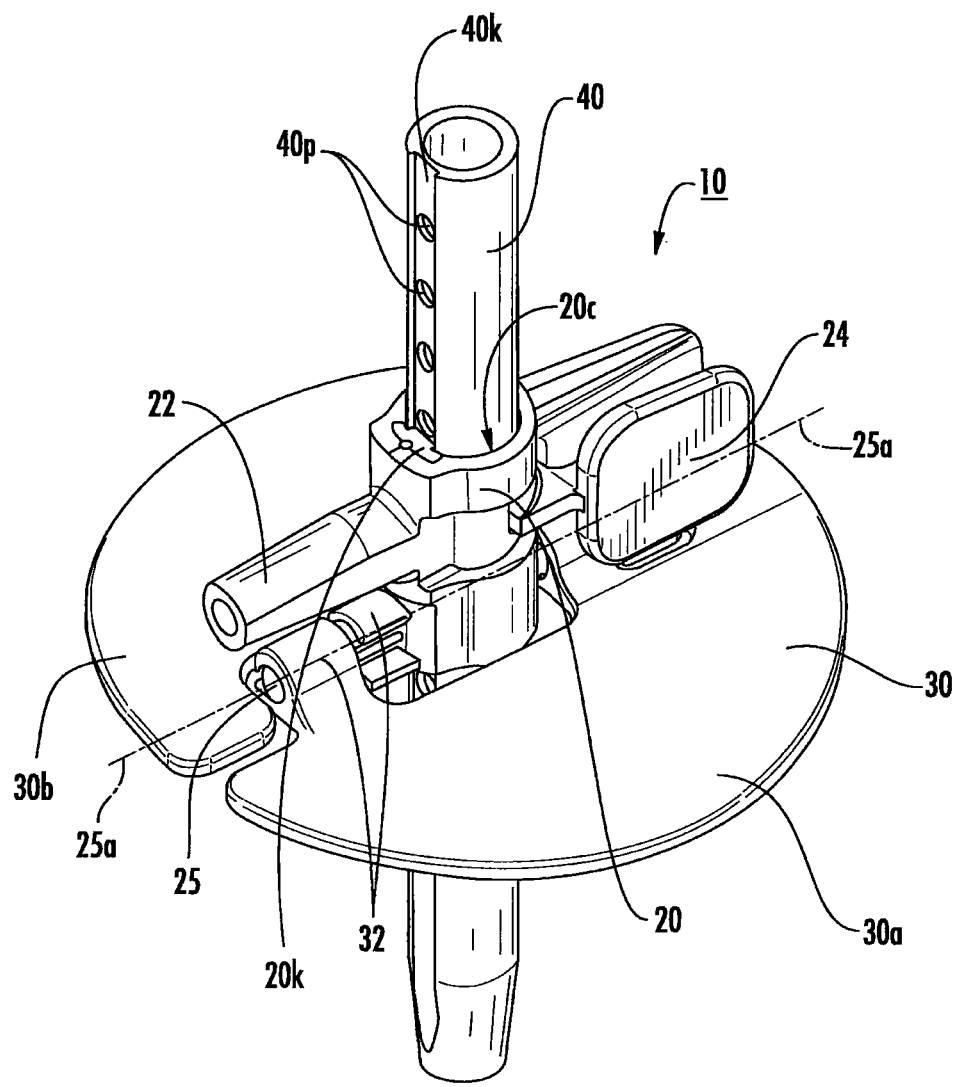
FIG. 1B is a side perspective view of another embodiment of the guide cannula and stabilizer according to embodiments of the present invention.
Figure 1C:
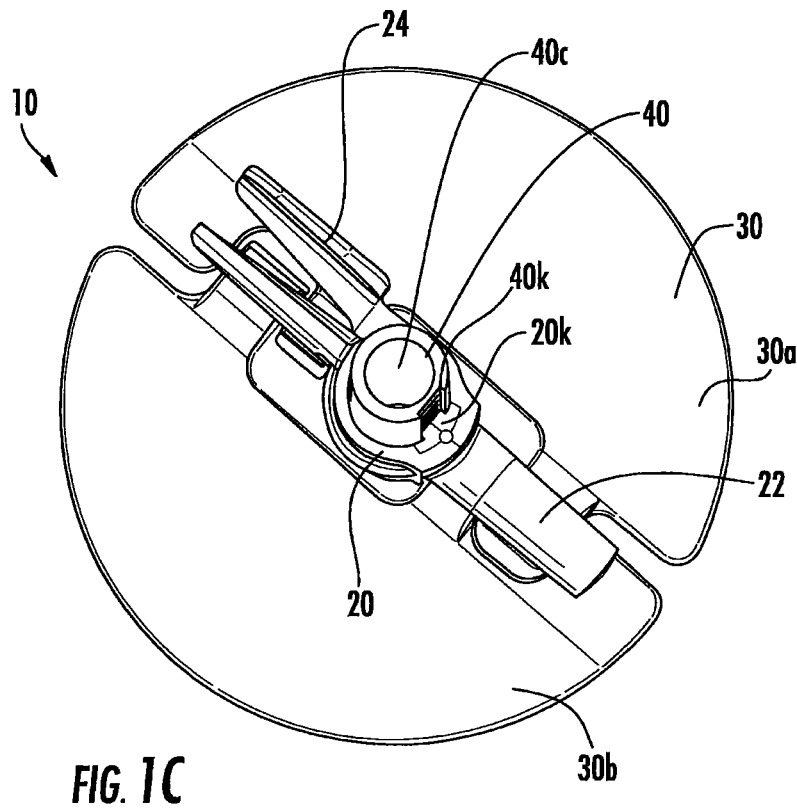
FIG. 1C is a top view of the guide cannula and stabilizer shown in FIG. 1B.

As shown in FIGS. 1A and 1B, for example, the tubular support member 20 can have a keyed alignment configuration where one member has a recessed key region and the other member has a protruding key region 20k, 40k, respectively, that, when aligned allow the two members 20, 40 to slidably engage and/or attach to prevent rotation about the longitudinal axis 20a while allowing the guide cannula 40 to be moved in a longitudinal direction relative to the tubular support member 20. FIG. 1A illustrates that the guide cannula 40 has a longitudinally extending protrusion segment as the keyed segment 40k and the tubular support member 20 has a recess as the keyed segment 20k. FIGS. 1B and 1C illustrate the opposite configuration, where the guide cannula 40 has a longitudinally extending recessed segment as the keyed segment 40k and the tubular support member 20 has the protruding, longitudinally extending segment as the corresponding keyed segment 20k. The guide cannula keyed segment 40k (protruding, FIG. 1A or recessed FIG. 1B) can hold the longitudinally spaced apart ports 40p.

Referring to FIG. 4, the hinge members 32 can include an arcuate upper wall segment 32a that resides above an arcuate channel 32c. The channel 25e can be configured to slidably hold a laterally extending arm 25 (which can also be described as "hinge arms"). The hinge members 32 can have a flat bottom surface 32f that resides against the skin of a patient. However, in other embodiments, the hinge members 32 can have other configurations and the bottom surface is not required to be flat or contact the skin of the patient.

In the embodiment shown in FIGS. 1A, 1B and 2-6A, the base 30 includes first and second base members 30a, 30b. The hinge members 32 allow the first and second base members 30a, 30b to move relative to the pivot/hinge axis 25a of the laterally extending arms 25 so as to be able to pivot up and down relative thereto. That is, the first and second base members 30a, 30b allow for independent angle correction on each side of the support member 20. It is contemplated that the first and second members 30a, 30b can allow the base to self-adapt and/or independently articulate to fit most size patients simply by pressing the base down or inward against the skin S of a patient.

The base 30 can have a circular perimeter as shown but can alternatively have other shapes. The first and second base members 30a, 30b can have semi-circular shapes, as shown in FIGS. 1A-6A, or may have other perimeter shapes. The base body can be solid as shown or may include apertures or channels.

Figure 3A:
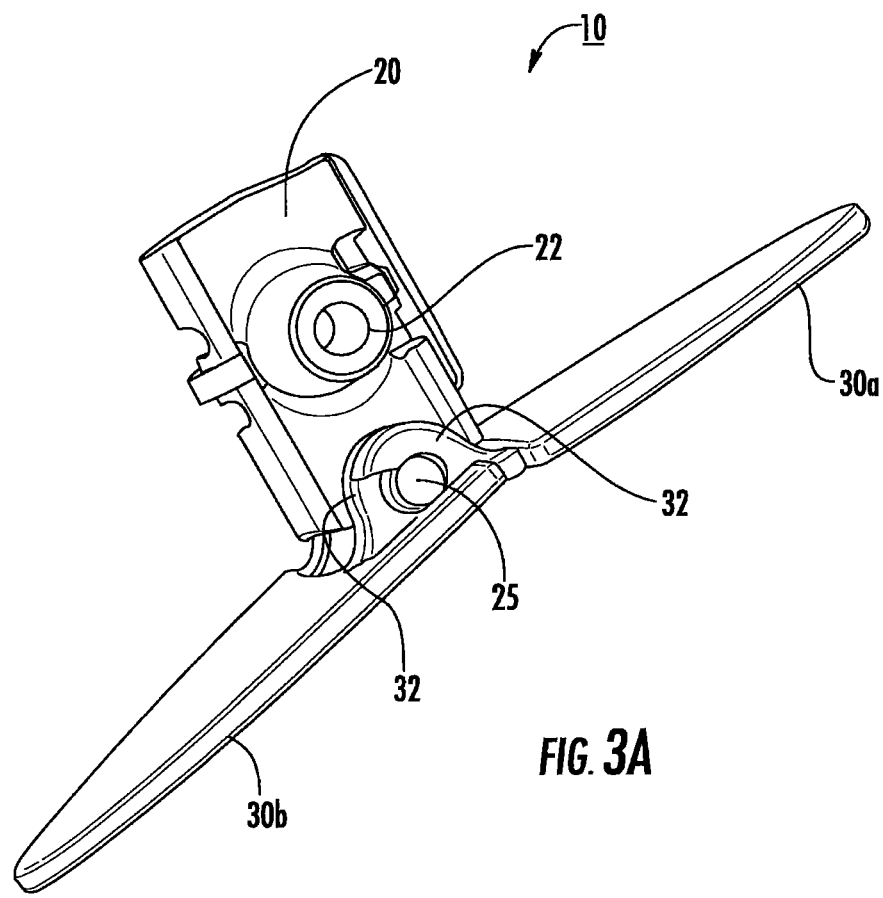
FIG. 3A is a side view of the stabilizer shown in FIGS. 1A and 1B according to embodiments of the present invention.
Figure 3B:
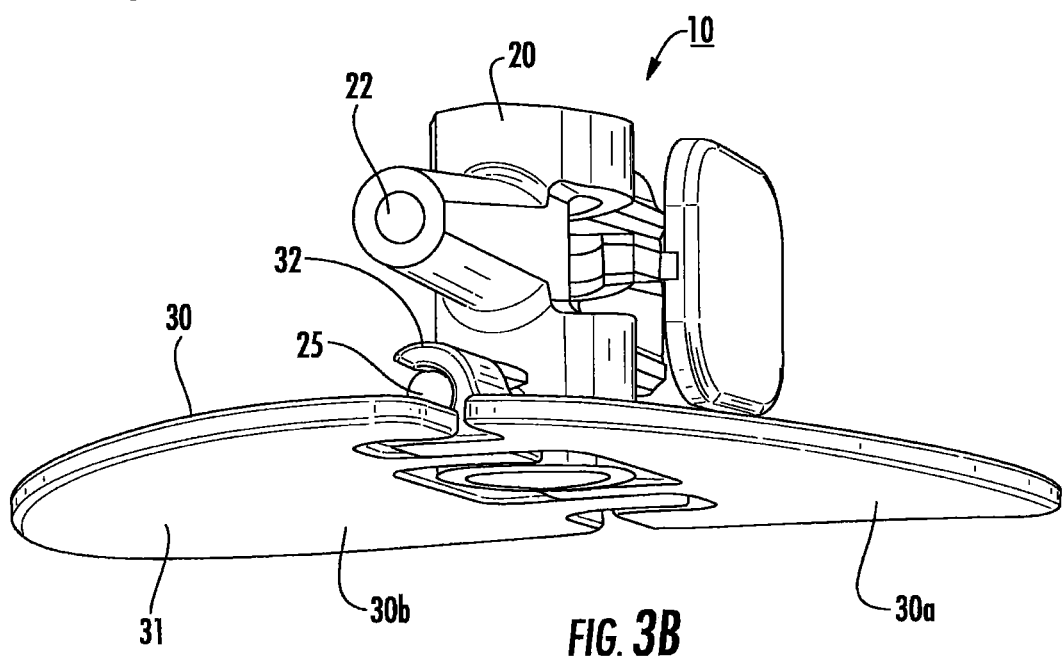
FIG. 3B is a side, bottom perspective view of a stabilizer similar to that shown in FIG. 3A, but illustrating a curved base according to embodiments of the present invention.
Figure 3C:
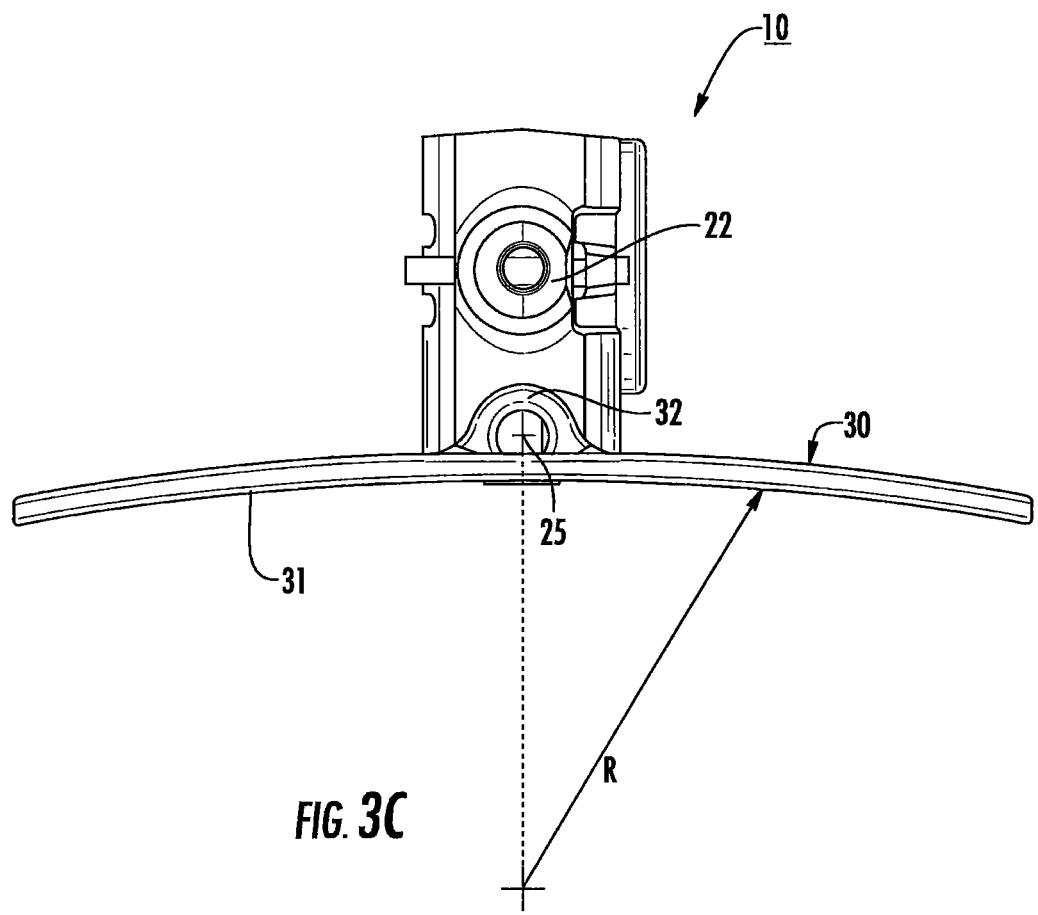
FIG. 3C is a side view of the stabilizer shown in FIG. 3B according to embodiments of the present invention.

As shown in FIGS. 3B and 3C, the base 30 can be curved in a direction facing skin of a subject, rather than planar as shown in FIG. 3A, for example. The base 30 can have a bottom 31 that has a radius of curvature R. The radius of curvature R can be measured from a center point that is in-line with an axial extending centerline of the tube 20 that extends down a distance below the tube itself. The radius of curvature R can be between about 4 inches to about 12 inches with any integer and/or fractional value therebetween. For example, the curvature R can be about 4 inches, about 4.5 inches, about 5 inches, about 5.5 inches, about 6 inches, about 6.5 inches, about 7 inches, about 7.5 inches, about 8 inches, about 8.5 inches, about 9 inches, about 9.5 inches, about 10 inches, about 10.5 inches, about 11 inches, about 11.5 inches, and about 12 inches. Although only illustrated for the base with the cooperating first and second members 30a, 30b, the same curved shape(s) can apply to the unitary base shown in FIGS. 7 and 8A-8E.

The first and second base members 30a, 30b can each have (right and left or top and bottom side) hinge members 32 and each can have an asymmetrical shape such that one outermost forward facing ("forward" referring to a direction facing the tubular support member 20) side has a different configuration from the other, with one side having a forward facing segment 33 that extends a distance in front of the hinge axis 25a and the opposing side has a forward facing segment 34 that resides behind the hinge axis 25a.

The first and second base members 30a, 30b can each include hinge members 32 that attach to the arms 25 of the support member 20. As shown, each of the first and second base members 30a, 30b includes a first hinge member 32 that reside adjacent each other on a common first arm 25 and a laterally spaced apart second hinge member 32 that reside adjacent each other on the other (second) arm 25. However, as noted above, the first and second base members 30a, 30b may include the laterally extending attachment arms 25 and the tubular body 20 can have the hinge members 32.

Figure 5B:
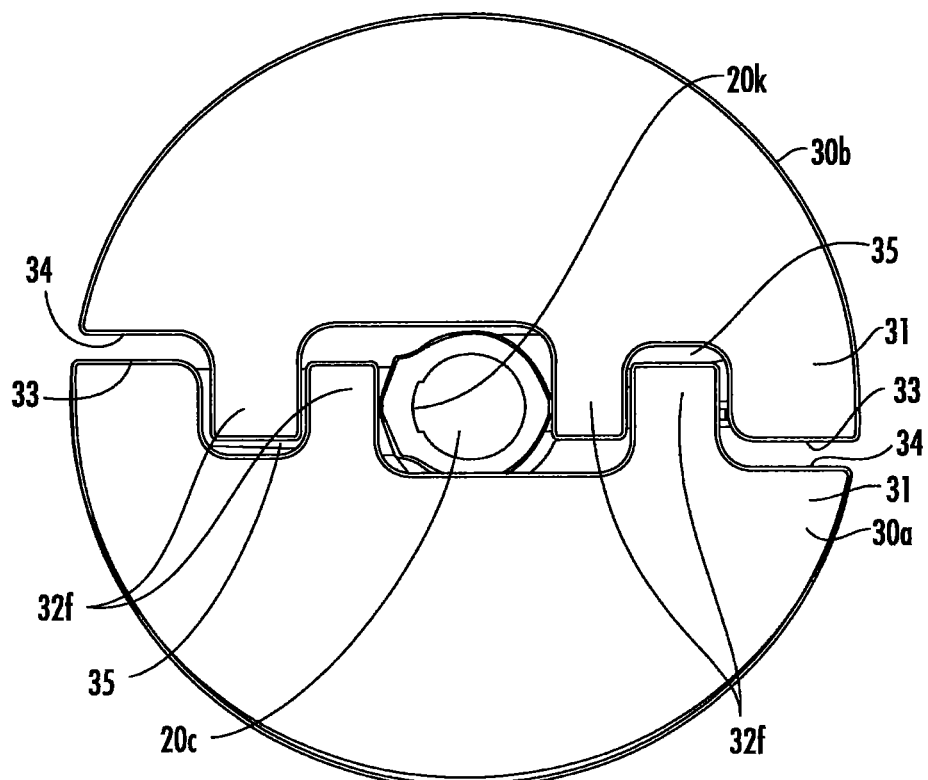
FIG. 5B is a bottom view of the stabilizer shown in FIG. 5A.
Figure 5C:
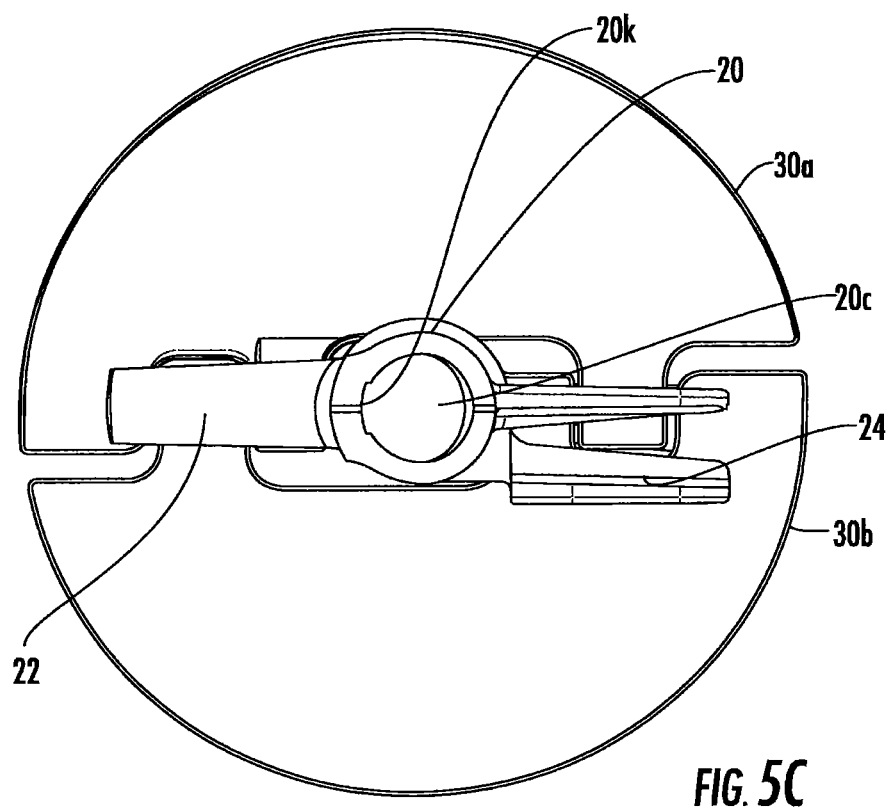
FIG. 5C is a top view of the stabilizer shown in FIG. 5A.

In some embodiments, the first and second members 30a, 30b are mirror images of each other so that the same part can be molded and used in cooperating pairs to reduce tooling costs. The base members 30a, 30b can include a forward facing side segment 33 that extends laterally spaced apart from one hinge member 32 with an open channel 35 between the hinge member 32 and forward facing side segment 33. The open channel 35 of a respective base member 30a and 30b can configured to receive a hinge member 32 of the other base member 30b, 30a as shown in FIGS. 5A and 5B, for example.

Figure 2:
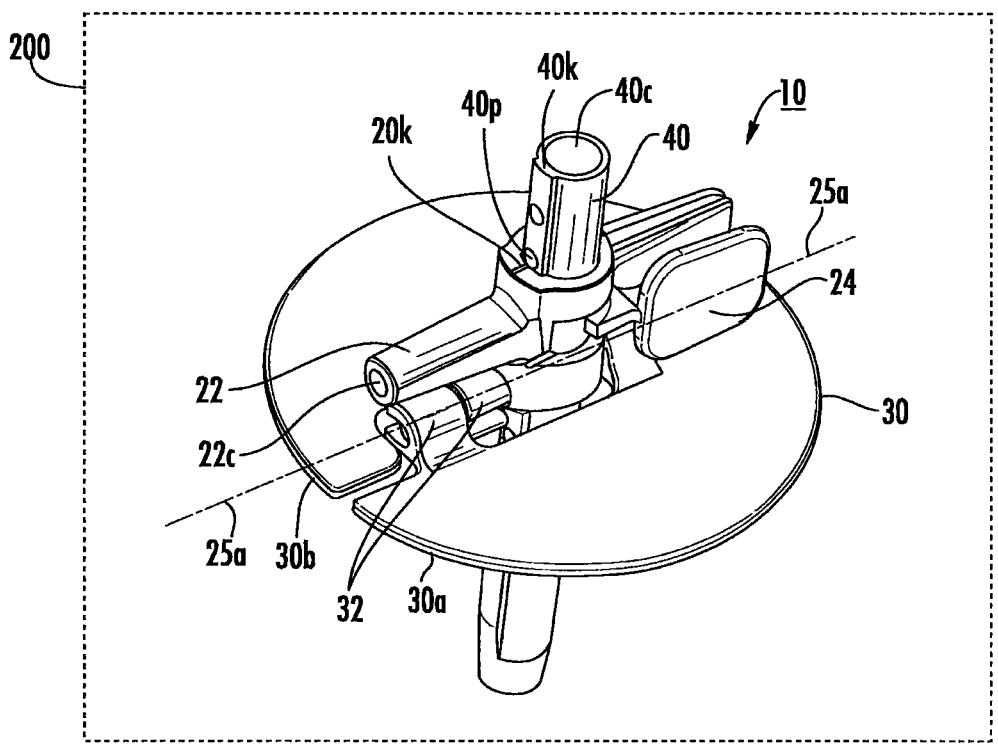
FIG. 2 is a top perspective view of the guide cannula and stabilizer according to embodiments of the present invention.

As shown in FIGS. 1A, 1B and 2, the tubular support member 20 can slidably engage a guide cannula 40 and/or other tubular device. In some embodiments, the guide cannula 40 can include a longitudinally extending open channel 40c and a wall 40w. The guide cannula 40 may include at least one open port 40p, shown as a plurality of longitudinally spaced apart, typically aligned, ports.

Figure 10:
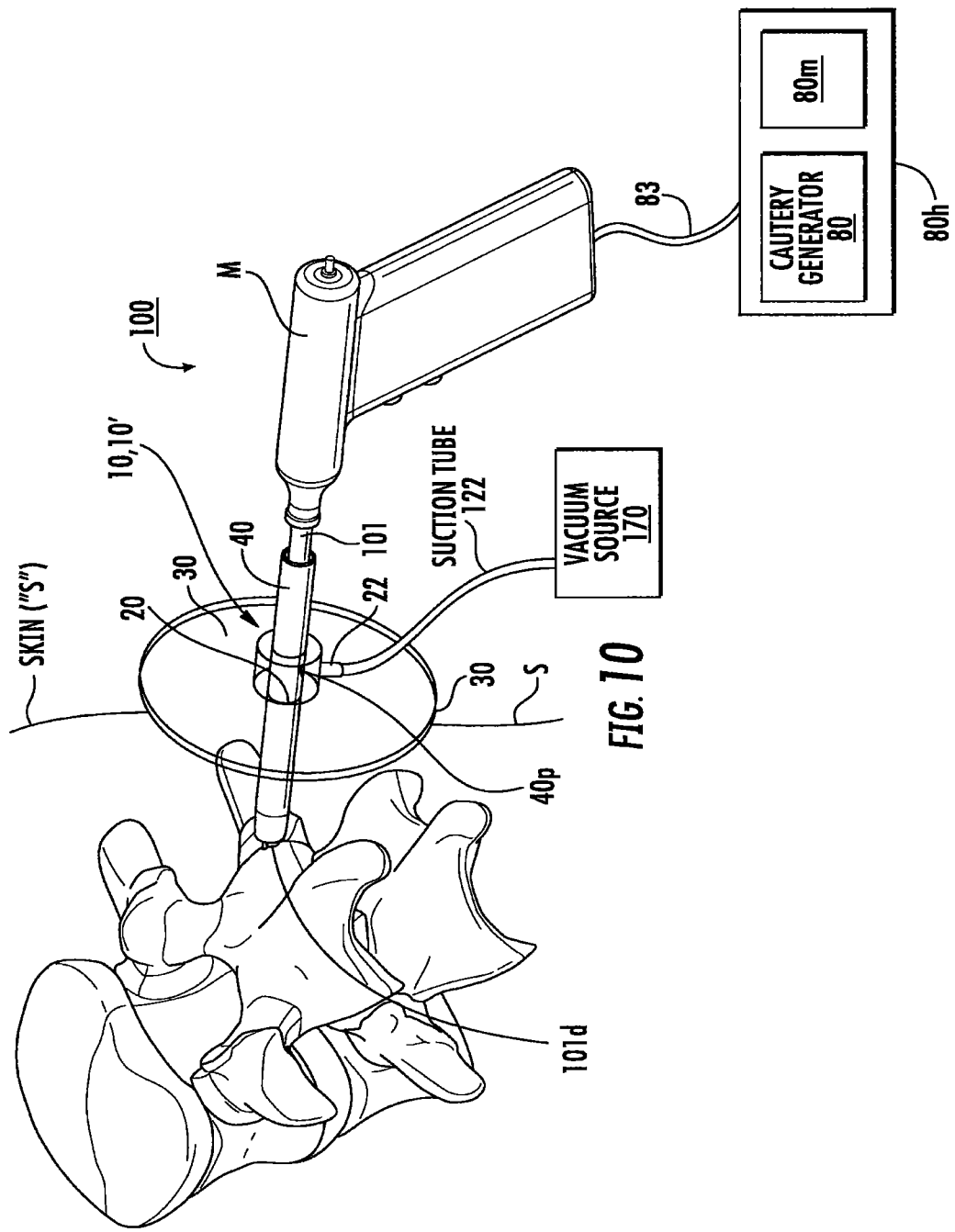
FIG. 10 illustrates a surgical tool inserted into the tubular support member to allow the surgical tool to pivot with the tubular support member relative to the stabilizer base (the distal end of the surgical tool is shown in line with a target spinal facet joint, by way of example) according to embodiments of the present invention.

As shown schematically in FIG. 2, the stabilizer 10 may be provided as a kit 200 which may optionally also include the guide cannula 40 and/or tool 100 (FIG. 10). The stabilizer 10 may be provided in an assembled or non-assembled state.

The guide cannula 40 (which may be described as a "portal" device) can be configured to allow a surgical tool or tools, e.g., an elongate barrel and/or shaft 101 (FIGS. 10, 11) of a (e.g., electro-cautery) tool 100 (FIG. 10), to be inserted therethrough into a body of a patient to position a distal end 101d at a target surgical site. See, e.g., co-pending U.S. patent application Ser. Nos. 14/257,490 and 14/810,683, the contents of which are hereby incorporated by reference as if recited in full herein, for examples of suitable tools for spinal facet treatments.

The tubular support member 20 can include at least one laterally outwardly projecting arm 22 with a fluid channel 22c and port 22p. The fluid channel 22c can reside above the laterally extending base attachment/hinge arms 25. The fluid channel 22c can have an axially extending centerline that is above and parallel to the hinge axis 25a. The arm 22 with the fluid channel 22c can have a length that is greater than the hinge arms 25. As shown in FIG. 10, conduit 122 can be attached to the arm 22 and a vacuum source 170 so that fluid and/or tissue, typically hot air, can be removed from the surgical site via a guide cannula port 40p that is aligned with and/or in fluid communication with the support member fluid channel 22c.

As shown in FIGS. 1A-6, the tubular support member 20 can also include finger grips 24 that extend laterally outward. The finger grips 24 can be circumferentially spaced apart from the arm 22 with the fluid channel 22c, typically at between about 30-270 degrees from the arm 22, such as about 45, about 90, about 180 or about 270 degrees (shown as at about 180 degrees offset from the arm 22).

Referring to FIGS. 1A, 1B and 2, the tubular support member 20 of the stabilizer 10 can be sized and configured to snugly hold the guide cannula 40 while allowing a user to adjust a height of the tube 40 to allow a desired length to extend below the stabilizer base 30. The term "snugly" means that there is frictional engagement between the two components so that the two components do not freely slide with respect to each other and/or the two components are held stationary relative to each other so as to remain in a fixed position absent a sufficient applied force to push or pull the guide cannula 40 relative to the support member 20. The guide cannula 40 can be slidably adjusted relative to the support member 20 for a desired longitudinal height position to place the distal end thereof at a desired intrabody position using a suitable (typically manual) force to push or pull the guide cannula 40 relative to the support member 20 for height adjustment and/or removal.

The tubular support member 20 of the stabilizer 10 can snugly hold the guide cannula 40 in a desired height position. The tool shaft 101 (FIGS. 10, 11) can be snugly or freely held inside the channel 40c of the guide cannula 40. This height can be selected/adjusted by a user so as to allow a user to adjust where the stabilizer support 20 holds the tube 40 thereby adjusting the height of the device 40 inside a patient body and/or below the bottom of the stabilizer base 30. The shaft or barrel of the surgical tool 100 (FIG. 10) can extend through the open channel 40c lumen of the guide cannula 40 while the guide cannula 40 is held in a desired height position by the stabilizer tubular support member 20.

FIGS. 7 and 8A-8E illustrate another embodiment of the stabilizer 10'. In this embodiment, the base 30' has a single piece design, e.g., it has a unitary or monolithic configuration. The base 30' has first and second hinge members 32, spaced apart across an open space 30s.

Figure 7:
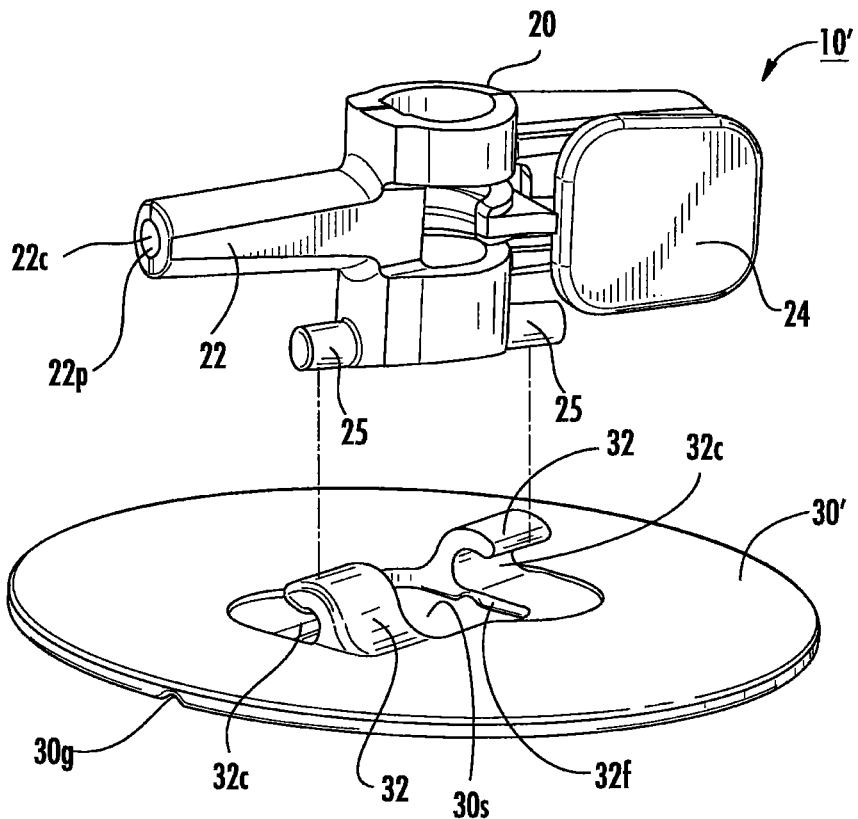
FIG. 7 is an exploded view of another embodiment of a stabilizer according to embodiments of the present invention.
Figure 8A:
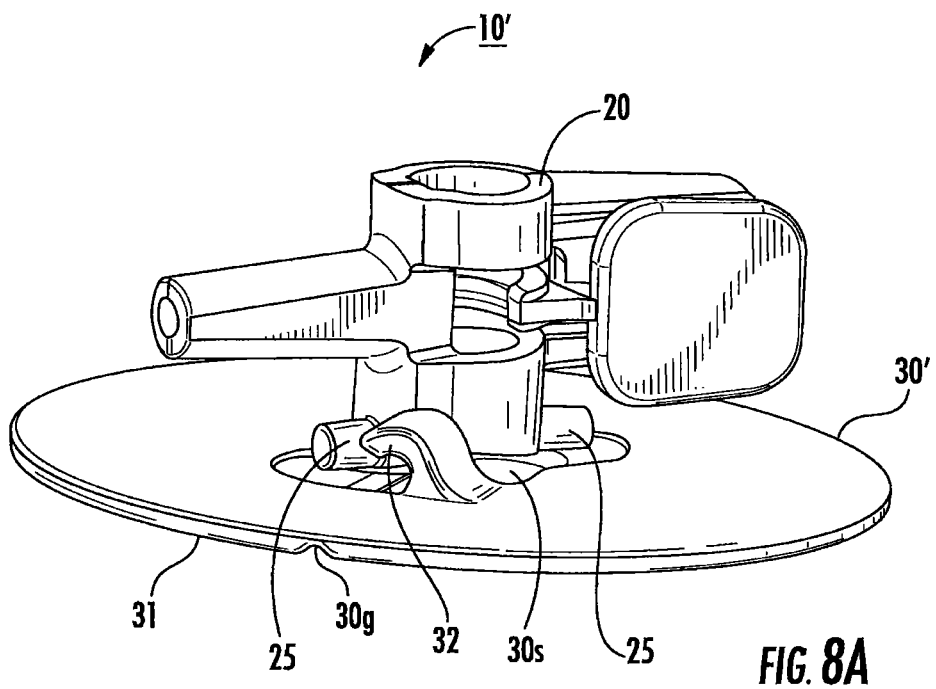
FIG. 8A is a side perspective view illustrating an exemplary assembly sequence to attach the base to the tubular support member of the stabilizer shown in FIG. 7 according to embodiments of the present invention.
Figure 8B:
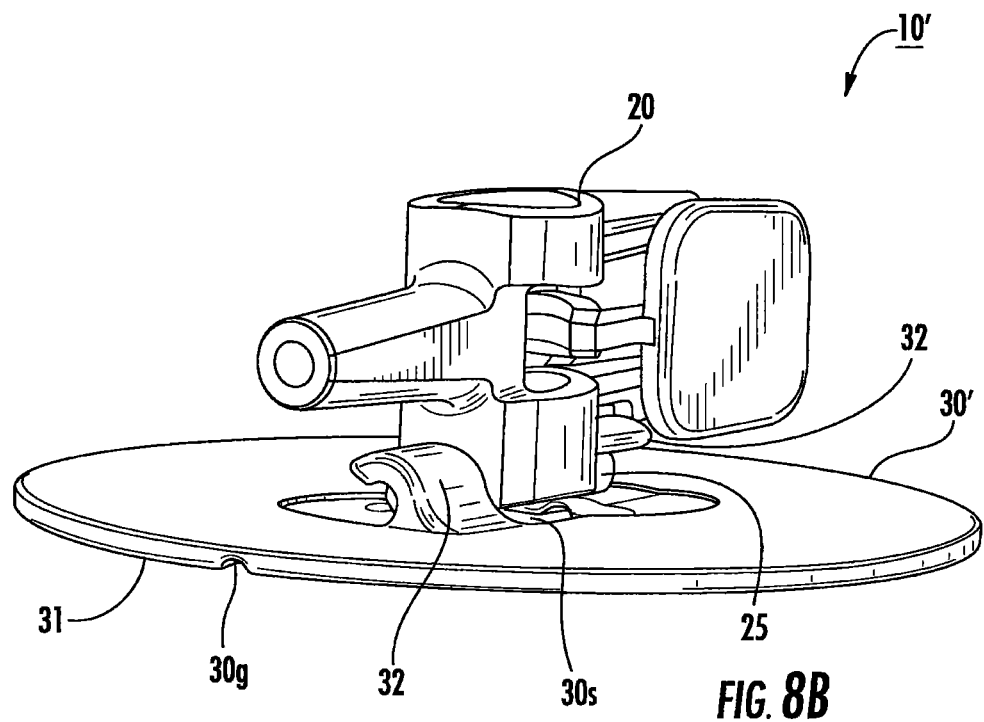
FIG. 8B is an assembled, side perspective view of the device shown in FIG. 8A.
Figure 8C:
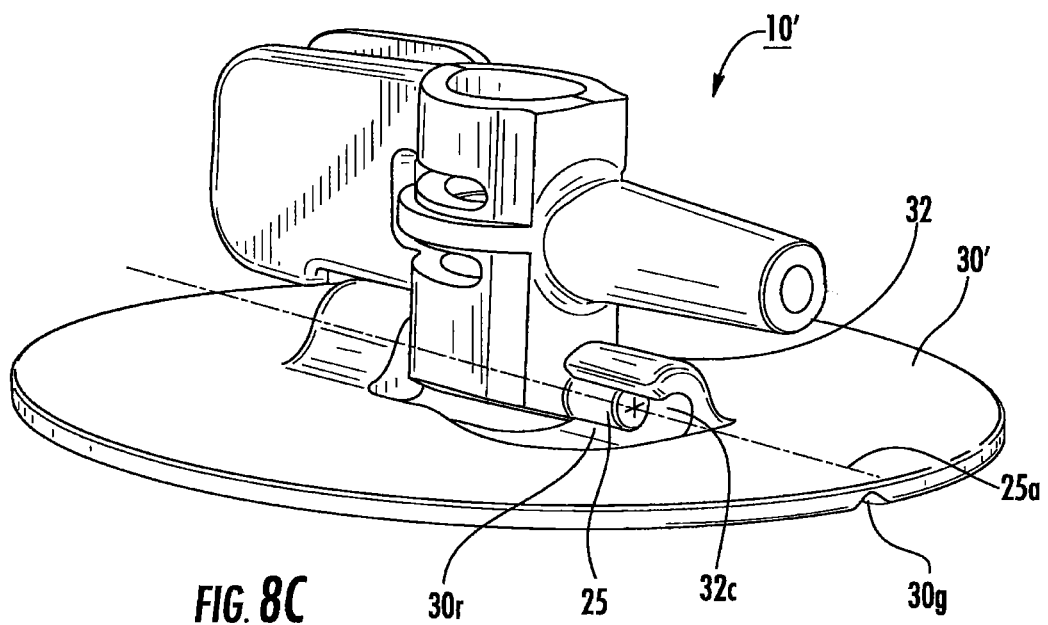
FIG. 8C is an enlarged side perspective assembled view of the device shown in FIG. 8B.
Figure 8D:
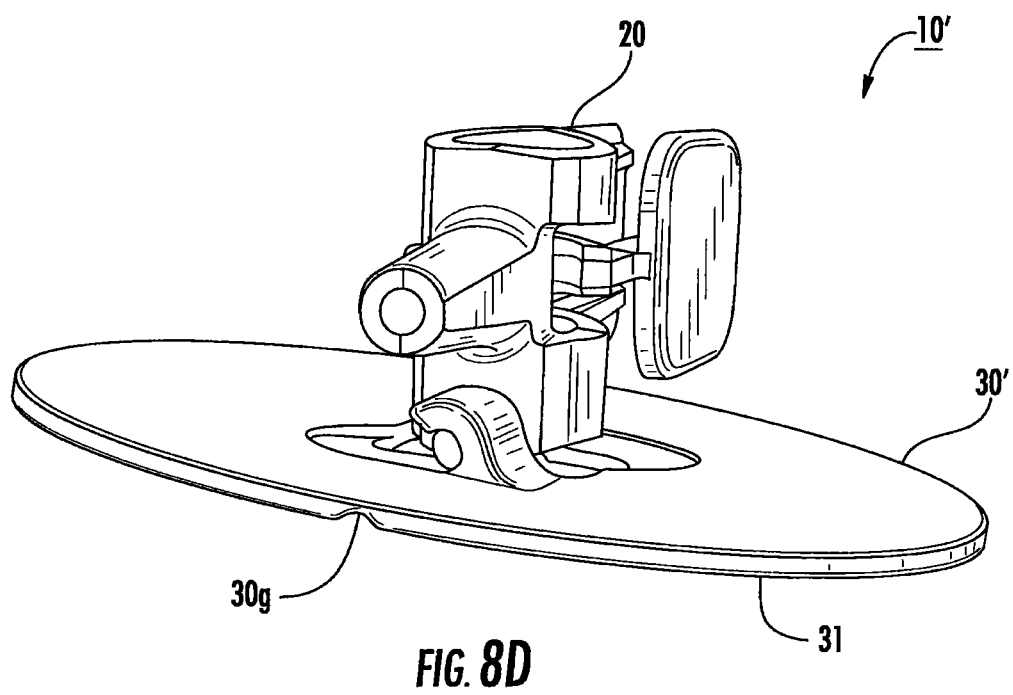
FIG. 8D is an enlarged side perspective assembled view, taken at about 90 degrees from the orientation shown in FIG. 8C.
Figure 8E:
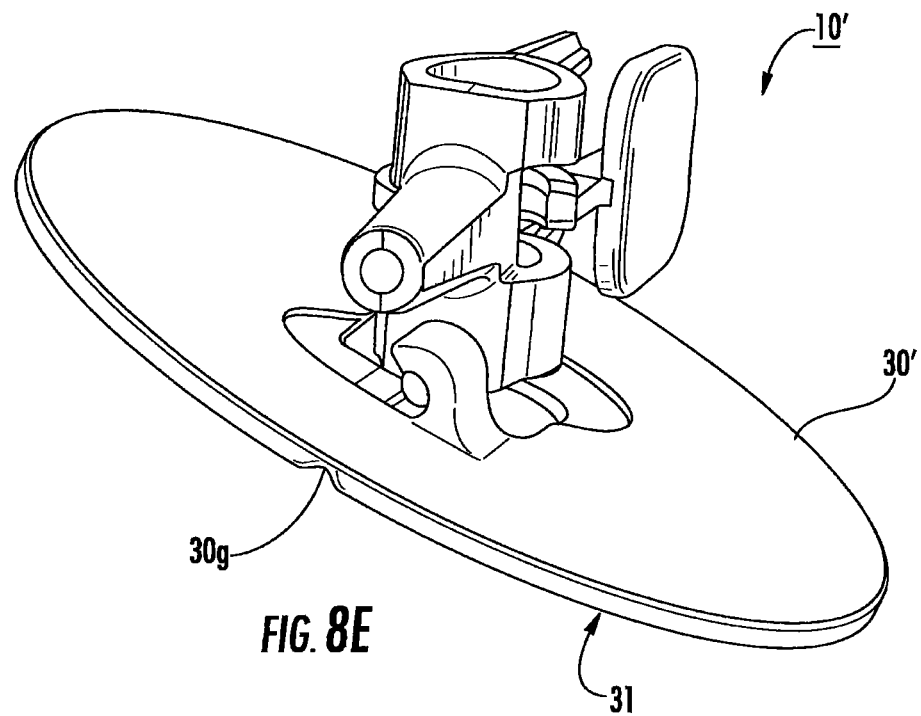
FIG. 8E is a side perspective view of the device shown in FIG. 7 illustrating the pivoting attachment between the tubular support member and base according to embodiments of the present invention.

As shown in FIG. 7, the tubular support member 20 can be positioned so that the attachment arms 25 are under the hinge members 32, then, as shown in FIG. 8A, the tubular support member 20 and/or the base 30' can be rotated so that the attachment arms 25 engage the hinge members 32.

As shown in FIGS. 8A-8E, the base 30' can include a bottom surface 31 with a groove 30g that extends across a center of the primary base body. The groove 30g can define a thinner segment of the base body. The groove 30g may be configured to allow the opposing sides of the base body to flex inwardly and/or articulate to contact a patient, typically partially or totally independent of each other, e.g., one side may extend at a different angle under the support member 22 against the skin of a patient relative to the other side. The groove 30g can be under and aligned with the hinge axis 25a or may be offset a distance such as between about 1-10 mm, for example.

Figure 9:
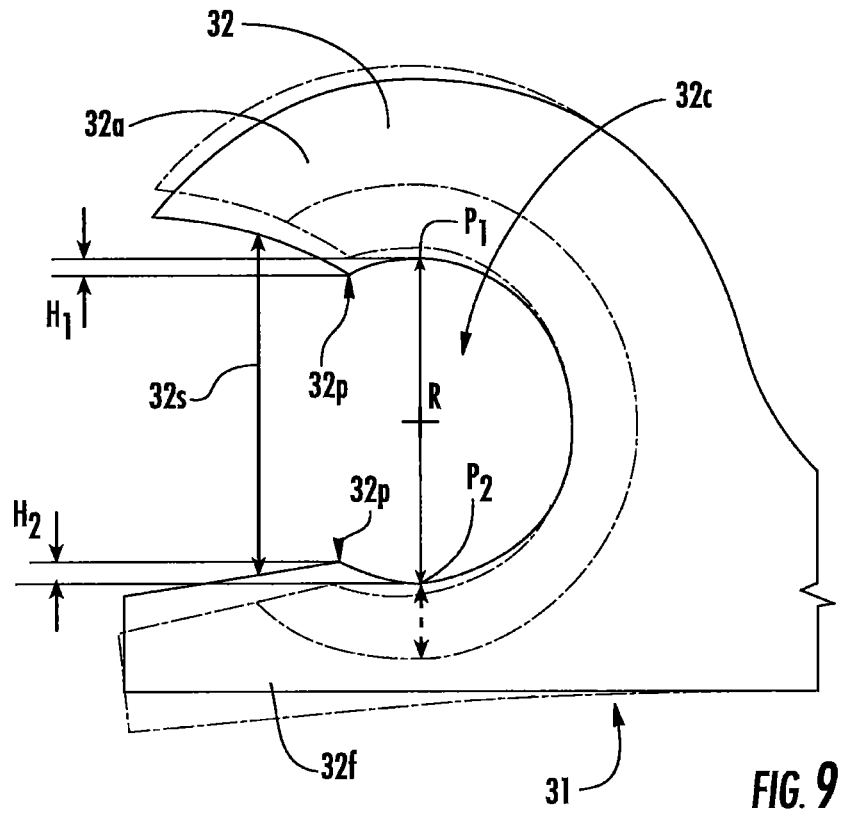
FIG. 9 is a schematic illustration of an exemplary shape of the shoulders of the stabilizer base shown in FIG. 7 according to embodiments of the present invention.

FIG. 9 illustrates that the hinge members 32 can have an upper arcuate segment 32a and a lower flat segment 32f as discussed above. The channel 32c can have a radius of curvature R that corresponds to a radius of the attachment arm 25. The hinge members 32 can have an open perimeter segment 32s that allows the base 30' to be attached to the tubular support member 20. The hinge members 32 can be configured to have suitable structural integrity to facilitate a suitable frictional pivoting engagement with the arms 25. The hinge members 32 can have a channel 32c with end segments residing a distance below a contact point of the radius of curvature to allow for suitable capture configurations while also allowing for assembly. The capture points 32p can reside a distance $H_1$ below a top perimeter and a distance $H_2$ above a bottom perimeter contact location $P_1$, $P_2$, respectively, associated with the radius of curvature R of the channel 32. $H_2$ is typically greater than $H_1$. $H_2$ can be about 0.010 inches and $H_1$ can be about 0.008 inches, in some embodiments. $H_2$ can be 0.010 inches and $H_1$ can be 0.008 inches, in some embodiments.

Referring to FIG. 10, embodiments of the invention provide stabilizers 10, 10' that cooperate with guide cannulas 40 and surgical tools 100 to allow for relative movement between the stabilizer base 30 and the guide cannula 40 and tool shaft 101. In some embodiments, the tool shaft 101 can pivot from side-side to allow for spinal facet joint debridement to remove the end plate receptor region which includes the synovial capsule and outer surface of the joint. Once the synovial capsule and outer surface of the joint are denuded, the nerves have nowhere to re-adhere to the joint and thus the joint is permanently denervated (communication between the facet joint and the brain is gone). In studies carried out by one of the inventors, pain relief is permanent in 75-80% of patients. While the joint continues to have arthritis, the patient's perception of the pain is gone as pain is what the brain perceives it to be and the patient simply does not feel the spinal pain. The joints have no worse decay then they would with the currently utilized RFL procedure since both utilize a denervation technique where the pain signals are severed between the brain and the joint.

Figure 11:
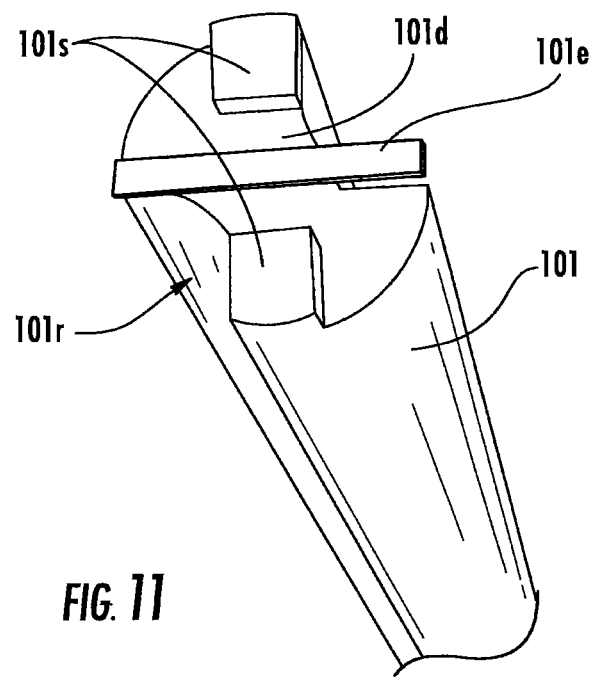
FIG. 11 is a greatly enlarged end perspective view of a rotatable shaft of a surgical tool with a cautery element forming a combination tissue removal (denudement) and cauterization tool for use with the stabilizer according to embodiments of the present invention.

With reference to FIGS. 10 and 11, the spinal facet therapy delivery tool (e.g., "debrider" tool) 100 has a shaft 101 with a distal head 101d that contacts target tissue and the head 101d is rotatable for denudement of the target tissue. As shown in FIG. 10, the tool 100 can connect to a cautery generator 80 to provide cautery power to a cautery element 101e (FIG. 11).

The cautery generator 80 can be any appropriate power, electro-surgery generator including third party generators and/or a custom generator that is dedicated for use in spinal facet surgery, e.g., configured for use only with the tools 100. If third party generators are used, the tool 100 can include a control circuit that can communicate with a selected generator input so as to be able to operate with multiple different generators. For example, a computer look up table can provide a selection of different defined generators 80 and the control circuit can be used to provide the appropriate settings, automatically or for manual adjustment. The generator 80 may optionally be provided as a custom generator with the tool 100 or made available from an authorized supplier according to defined specifications of operation to meet regulatory guidelines for medical use and comply with Good Manufacturing Practices, for example.

In some embodiments the cautery generator 80 can be provided in a unit or housing 80h that also holds the motor power source 80m for the motor M that rotates the shaft 101 so that the tool 100 can have an electrical connection to the combination unit for powering both functions during a medical procedure (FIG. 10). The unit 80h can thus provide cautery power to the surgical tool 100 and electrical power to the tool 100 for the rotational motor M of the device shaft or barrel 101. Having the generator unit 80h provide both the cautery and electrical power generation can eliminate the batteries for power the rotational motor to be held onboard the body of the tool.

After a defined active cauterizing time, e.g., between about 10-30 seconds of active cauterizing time, with an exemplary cautery site temperature of about 302 degrees F., the vacuum port 22*p*, cooperating with the guide cannula 40, can be configured to vent heat from inside the guide tube 40 to outside the patient body and maintain a maximum temperature inside the guide cannula 40 to about 122 degrees Fahrenheit (degrees F.) (e.g., no greater than +2 degrees) or lower, e.g., typically below 122 degrees F. and at or above about 80 degrees F. Animal laboratory testing or cadaver testing can be used to test the max temperature using the vacuum port 22*p* on the stabilizer 20 and cooperating guide tube 40 with the cauterizing surgical tool 100. The target safe temperature for humans (away from the cautery site) is about 122 degrees F.

FIG. 10 illustrates a tool 100 with the barrel or shaft 101 which is rotated by an onboard motor M). The tool 10 can include a cord or cords 83 that connect to the cautery generator housing 80*h*.

Referring to FIGS. 1A, 1B, 1C and 2, the ports 40*p* can be longitudinally spaced apart along a length of the guide cannula 40. Although shown as vertically aligned, they may be laterally offset and may be clustered rather than regularly spaced apart. Also, although shown as a plurality of ports 40*p*, the cannula 40 may include a single port 40*p*. Although shown as a single fluid channel 22*c* multiple channels can be provide in the same arm 22 or in different arms or other shaped components.

Still referring to FIGS. 1A, 1B and 2, in some embodiments, the ports 40*p* may be provided in a closed state prior to user selection of a desired port or ports for a particular procedure or patient. The ports 40*p* may include a sealant or cover that is thermally suitable that attaches to an inner and/or outer wall of the guide cannula 40 and extends over one or more of the ports 40*p*. The ports 40*p* may be preferentially scored but intact so as to be sufficiently sealed to inhibit gas exhaust when intact. The ports 40*p* can be substantially or totally sealed with thinner wall perimeter segments that can be detached to expose a port to allow a user to push open a desired port 40*p* during or prior to a procedure.

It is preferred, but not required, that the port 40*p* that is used for a procedure align longitudinally and laterally with the fluid channel 22*c*. However, the ports 22*c*, 40*p* may be misaligned as long as there is sufficient fluid communication to provide for heated exhaust gases to be removed to keep the temperature in the guide cannula 40 (at least the part that is in the patient body and proximate the skin S) below at 122 degrees F. or below.

In preferred embodiments, the wattage of the cautery generator is between about 40 Watts to about 50 Watts, which is much less than maximum wattages that many surgical cautery generators can provide.

In some embodiments, the head 101*d* (FIGS. 10, 11) can have an electro-conductive member and/or outer surface 101*e* to which electrical energy is supplied (in bipolar or monopolar mode, typically monopolar mode), thereby permitting the head 101*d* to cauterize tissue. The electro-cauterization can be any suitable cautery source 80, typically RF power, although other electrical sources may be used. For additional discussion of components of a suitable combination spinal facet debrider tool 10, see, e.g., U.S. Pat. No. 8,167,879; and co-pending U.S. patent application Ser. No. 14/257,490, the contents of which are hereby incorporated by reference as if recited in full herein.

The distal end portion of the therapy delivery tool 101*d* can have a maximal outer diameter that is between about 5-15 mm, such as about 5 mm, about 6 mm, about 7 mm, about 8 mm, about 9 mm, about 10 mm, about 11 mm, about 12 mm, about 13 mm, about 14 mm and about 15 mm, typically between 10-12 mm.

Procedures with which embodiments of the present invention are utilized can be done via conscious sedation and local anesthesia or general anesthesia as per the surgeon's and patient's preference. For, example, conscious sedation can be used with a remifentanyl mixture. The spinal region is typically prepped and draped accordingly. Utilizing fluoroscopic or other suitable imaging guidance, the facet joints J that may be treated can be identified.

The base 30, 30' can have a bottom with a width that is between about 2-6 inches, typically between about 3-5 inches, such as about 3 inches, about 3.5 inches, about 4 inches, about 4.5 inches and about 5 inches. The stabilizer tubular support member 20 typically has a smaller height than the height of the shaft 101 (FIG. 10, 11) of the therapy delivery tool 100 and/or height of the guide cannula 40. In some particular embodiments, the stabilizer tubular support member 20 can have a height that is between about 2-10 inches, typically between about 3-6 inches, such as about 3 inches, about 3.5 inches, about 4 inches, about 4.5 inches, about 5 inches, about 5.5 inches, and about 6 inches, although the stabilizer tubular support member 20 may have other height dimensions.

As shown in FIGS. 1A, 1B and 2 the stabilizer 40 can releasably, slidably engage the guide cannula 40. The stabilizer tubular support member 20 can be configured to releasably lock against an outer surface of the guide cannula 40. The locking engagement can be provided using a physical lock member (e.g., a clamp or other suitable lock) or a locking configuration, e.g., frictional engagement or other locking configuration. The stabilizer support member 20 and cannula 40 engagement can be through any suitable physical engagement that allows the stabilizer support member 20 to lock against the cannula 40 directly or indirectly and preferably also allows for the height adjustment of the cannula 40 in the stabilizer support member 20.

The therapy device 100 can be configured such that when the elongate barrel 101 and/or shaft is inserted fully through the guide cannula 40 in an operative configuration, the head and/or distal end of the therapy device 101*d* extends beyond the front or distal end of the cannula 30 only by between about 2 mm to about 7 mm, such as about 2 mm, about 2.5 mm, about 3 mm, about 3.5 mm, about 4 mm, about 4.5 mm, about 5 mm, about 5.5 mm, about 6 mm, about 6.5 mm or about 7 mm. Thus, the stabilizer tubular support member 20 can lock the cannula 40 in a longitudinal position and the stabilized/locked position of the cannula 40 relative to the skin of the patient S based on the stabilizer 10, 10' keeps the distal end of the barrel or shaft 101*d* at the target site and can act as a stop to keep the head 110*d* from moving deeper into the body.

The stabilizer 10, 10' may optionally provide some structural support for the guide cannula 30 and/or tool 10 at the entry site. The stabilizer base 30, 30' can have a bottom that is thin, typically between about 1-10 mm, more typically between about 2 to about 4 mm. The bottom can be semi-rigid or rigid. The bottom 31 can be configured to conformably reside against the skin of the patient.

Optionally, the cannula 40 can slidably extend and reside over a dilation tube. The cannula 40 may be sized and configured to snugly reside against the dilation tube so that it does not freely slide along the dilation tube without pushing by a user. The guide cannula 40, held in the tubular support member 20, can be positioned upstream of the tapered end on the dilation tube 50 prior to inserting the dilation tube in the body. In other embodiments, the cannula 40 can be separately inserted over the dilation tube after the dilation tube 50 is inserted into the body. In any event, once the tapered end reaches the facet joint, the guide cannula 40 (e.g., working tube) can be pushed down to the facet joint J so that the distal end thereof resides at the facet joint. The dilation tube can then be removed, leaving the cannula 40 in position.

The guide cannula 40 and tubular support member 10 are typically rigid. The cannula 40 and stabilizer 10, 10' can be formed or include materials that may be compatible with autoclaving for sterilization. The cannula 40 and tubular support member 20 can be metallic or other non-toxic and/or biocompatible material that is sufficiently rigid and that may be high-temperature (autoclave) heat-resistant or suitable for the thermal exposure during cauterization. Other sterilization protocols may be used that do not require heat. The guide cannula 40 and tubular support member 20 can be metallic (and if so can have an electrically insulating material over an end portion or surface thereof) or may be polymeric or other plastic material with sufficient rigidity to provide the guide path for the tool 100. One exemplary material, by way of example only, is Polyether ether ketone (PEEK).

In some particular embodiments, the guide cannula 40 may comprise a stainless steel material with an inner surface having an electrically insulating material. The electrical insulating material can be configured to inhibit arcing with the electro-cautery output, e.g., RF energy at the head 101d, when the tool is configured to apply RF energy for the cauterization. The electrical insulating material can be provided by an internal sleeve or coating or otherwise. The insulating material may reside on only a distal end portion of the guide cannula 40 or over an entire inner surface of the cannula 40. The electrically insulating material may optionally reside on the outer surface of the guide cannula 40, such as on the distal end thereof.

The stabilizer 10, 10' can be positioned prior to, during or after insertion of a guidewire/pin (where used), the dilation tube and/or the cannula 40.

The tool head 101d can be rotated to denude tissue until bone at the target spinal facet joint is reached. In preferred embodiments, the rotation of the head 101d can be automatic using the motor M with a drive shaft 101 (FIG. 10). However, in some embodiments, the denudement head 101d can be manually rotated. The therapy tool head 101d can also configured to cauterize the soft tissue during and/or after the denuding.

As shown in FIG. 10, in some embodiments, the tool 100 can have an elongate barrel and/or shaft 101 with a length sufficient to reach the target intrabody spinal facet site. The length of the barrel and/or shaft 101 can be between about 100 mm to about 150 mm.

The guide cannula 40 can have a diameter that is slightly larger than the outer diameter of the tool barrel or shaft 101, e.g., between about 0.1 mm to about 1 mm to allow snug sliding entry of the tool 100. The tool 10 can have various form factors. The barrel 10b may rotate or be static. The drive shaft 101 and rotate with the head 101d as an integral or separate component thereof and the shaft 101 may be encased in a barrel housing allowing the head 110d to extend therefrom. The denuding of target soft tissue with the tool 100 can have a duration (with the active rotation of the debridement tool head) that is between about 30 seconds to about 3 minutes long, typically between about 30 seconds to about 2 minutes, on average. The tool 100 can be configured to continuously rotate the head 101d during both cauterization and subsequent (light) tissue scraping/cleansing upon contact with bone at the facet joint. In some embodiments, the tool 100 can be configured to discontinuously rotate the head 101d and/or interleave the cauterization with the rotation.

Once the soft tissue is denuded, the tool head 101d can be rotated with sufficient force and time to contact the outer surface of the bone under the denuded tissue for a desired short time, e.g., between about 10 seconds to about 2 minutes, more typically between about 10 seconds to about 60 seconds, to cleanse an exposed outer surface of the bone thereat substantially without removing bone. The short tissue cleansing/scraping time, post-cauterization (e.g., post-denuding), can be controlled with an auto-shutoff for the tool rotation and can be timed based on user or electronic (auto) shut off of the cautery/burn or based on sensor feedback of contact with bone.

The tool 100 can be rotated with the same rotational speed for the bone surface cleansing relative to the denuding action or with a different rotational speed and/or force for the bone surface cleansing relative to the denuding action. In some embodiments, the tool 100 has a first defined rotational speed range for the denuding and a different defined rotational speed range for the cleansing. The transition from denuding (with or without cauterizing) to cleansing can be automatic or manual. If automatic, a sensor can trigger the transition to a different speed and/or to terminate the power to stop the cauterizing action. If manual, a user interface (UI) via a control such as a switch or a voice prompt to a control circuit can direct the change in operation, e.g., slow rotation and stop cautery/burn.

In some embodiments, the tool 100 can be configured to apply the cauterization without rotation of the head 110d then cleanse/tissue scrape with the rotation of the head 101d. This may be particularly suitable for laser, ultrasound or cryo-ablation configurations.

The speed of the rotation of the therapy delivery tool head 101d (e.g., a tissue scraper and cautery head) can be relatively low to avoid cutting into the bone. Most orthopedic burrs will operate up to 60,000 rpm which can be hard to control and can dig into the bone. Thus, lower rotational speeds are desired for both the denuding and cleanse modes or action. The objective is to sweep the tissue off the bone and not drill into the bone during the cleanse mode. Thus, in some embodiments, for both denuding and cleansing of the bone, a speed of below about 5000 rpm may be appropriate, typically between about 10 rpm to about 5000 rpm, and more typically between about 10-1000 rpm. The speed may be different for the cauterizing and the tissue cleansing/scraping. In some embodiments, the speed is between about 10 to about 5000, including about 125 rpm, about 150 rpm, about 200 rpm, about 250 rpm, about 300 rpm, about 350 rpm, about 400 rpm, about 450 rpm, about 500 rpm, about 550 rpm, about 600 rpm, about 650 rpm, about 700 rpm, about 750 rpm, about 800 rpm, about 850 rpm, about 900 rpm, about 950 rpm, about 1000 rpm, about 1500 rpm, about 2000 rpm, about 2500 rpm, about 3000 rpm, about 3500 rpm, about 4000 rpm, about 4500 rpm and about 5000 rpm.

In some embodiments, the speed is low speed for one or both the denuding (with or without cauterizing) and the cleansing. The term "low speed" means between about 10 rpm to about 100 rpm, including about 10 rpm, about 15 rpm, about 20 rpm, about 30 rpm, about 40 rpm, about 50 rpm, about 60 rpm, about 70 rpm, about 80 rpm, about 90 rpm and about 100 rpm.

In some embodiments, the order of use of the components where the stabilizer 10, 10' is used can be: insert a guide pin, then insert a dilator tube. Next, the stabilizer 10, 10' can be placed on the skin S over the guide pin and/or dilator tube. The dilator tube can then be removed if it was used. The guide cannula 40 and/or therapy tool 100 can be inserted through the stabilizer 10, 10' with or without the guide pin in place (that is the guide pin, where used, can have been previously removed or removed after the cannula 40 and/or tool 100 are inserted through the stabilizer 10, 10'). The tool 100 can deliver the therapy to the facet joint with the pin in position and extending through a pin bore or the therapy to the facet joint can be applied after the pin is withdrawn.

The stop depth provided by the stabilizer 10, 10' and/or stabilizer and guide cannula 40 combination may be adjustable. The clinician can decide an appropriate stop depth for the patient prior to placing one or more of the components in the patient.

The stabilizer 10, 10' can also be placed on the skin S before or after the guide pin is inserted at the treatment joint. The entire tool 10 with the cable 13 can be sterile and single use disposable.

FIG. 11 also illustrates that the shaft 101 can be configured with a fluted configuration to inhibit tissue clogging during denuding or tissue scraping. The fluted configuration can have first and second curvilinear longitudinally extending recesses 101r that can extend over a major portion of a length of the shaft 101, typically over the entire length of the shaft 101. The distal end or head 101d of the shaft 101 can include first and second tissue scraping elements 101s that are positioned across from each other, with a linear cautery element 101e therebetween. The tissue scraping elements or members 101s can comprise a molded rigid polymeric material, such as Polyether ether ketone (PEEK) is a colorless organic thermoplastic polymer in the polyaryletherketone (PAEK) family, used in engineering applications. The tissue scraping elements or members 101s can be rectangular as shown, or may have other geometric shapes. The first and second tissue scraping members 101s can have the same or different shapes, but typically have the same projection distance relative to the cautery member 101e. The tissue scraping members 101s can be provided as only two or provided as one or more than two spaced apart components.

The flutes 101r can be straight or curvilinear. The flutes 101r can be thin, e.g., between about 1 mm to about 5 mm. The flutes 101r can extend longitudinally over a small portion of the length of the shaft and/or barrel, such as between about 3 mm to 1 inch, or over substantially a length of the shaft and/or barrel 101 sufficient to extend through the working cannula 40, e.g., a length between about 50 mm to about 200 mm, including about 50 mm, about 75 mm, about 100 mm, about 150 mm and about 200 mm.

The lateral dimension of the distal end of the shaft or head 101d can be between about 3-15 mm (if a non-expandable configuration is used) and between about 3-25 mm if an expandable version is used. In some embodiments, a maximal distal head lateral dimension with the flutes 101r can be between about 5-15 mm such as about 5 mm, about 6 mm, about 7 mm, about 8 mm, about 9 mm, about 10 mm, about 11 mm, about 12 mm, about 13 mm, about 14 mm, and about 15 mm.

The discrete electrocautery member 101e can be configured to slidably, longitudinally extend and retract relative to the adjacent non-conductive shaft or barrel 101 or may be statically affixed to same.

It is contemplated that the spinal facet debridement procedure with the combination debrider tool 100 can allow the spinal debridement procedure to be carried out by general surgeons, radiologist, pain medicine, physical medicine, orthopedic and neurosurgeons and/or allow more surgeons to be able to competently carry out the procedure thereby providing more global access to this treatment for patients with longer term pain relief and obviating the need for follow-up treatments upon nerve renervation at the treated spinal facet joint(s).

Embodiments of the invention provide treatment methods that can be carried out at an outpatient clinic and/or as an outpatient procedure at a hospital or surgery center.

Figure 12:
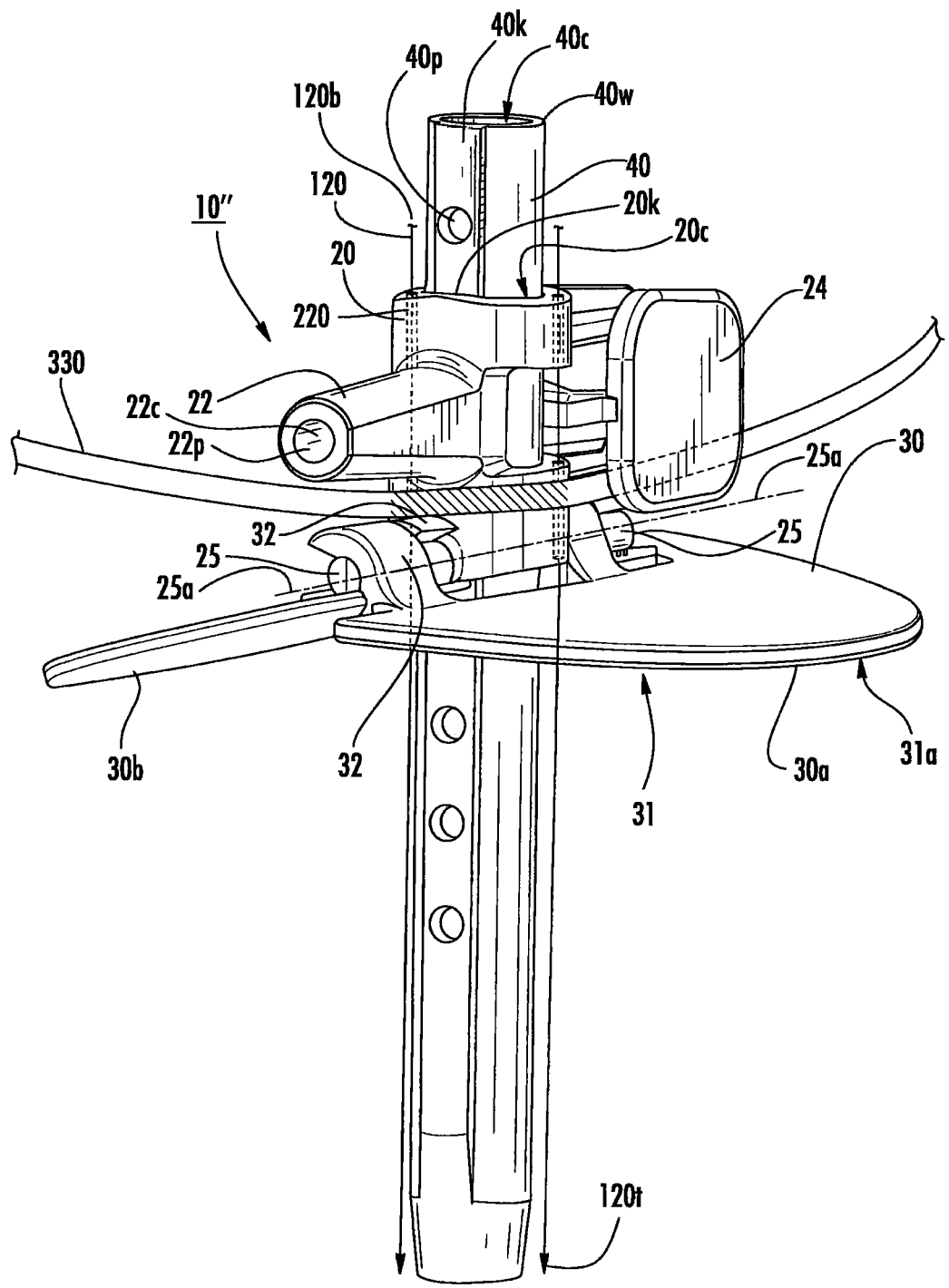
FIG. 12 is a side perspective view of another embodiment of a surgical tool comprising a guide cannula held by a cooperating stabilizer with optional supplemental components such as k-wires and/or stabilizer strap according to embodiments of the present invention.

FIG. 12 is a side perspective view of another embodiment of a surgical stabilizer tool 10" comprising a guide cannula 40 held by the cooperating tubular member 20 with one or more optional supplemental positional components such as a plurality of circumferentially spaced apart k-wires 120 and/or a strap 330 according to embodiments of the present invention. Where used, the base 30 can optionally include an adhesive 31a on the bottom 31 to releasably attach to skin of a patient as discussed above.

The strap 330 can include a ring segment 330r that can, in some embodiment, encircle the tubular support member 20. The strap 330 can moldably or adhesively attached to the tubular support member 20 or may be a separate discrete member secured to the tubular patient during a therapy session. The strap 330 can be overmolded to the tubular member 20. The strap 330 can be elastic, flexible or inelastic (not stretchable or stretchable by only about 10% when exposed to a manually applied pull force of 101bf) or combinations of same. The strap 330 can have a continuous length or may be provided in attachable segments. The strap 330 can have a length sufficient to extend under a patient's stomach when the patient is lying on a surgical table to provide a holding force against the strap 330 to inhibit side to side movement of the column support/portal tube 20 when attached. The strap 330 can extend to attach directly or indirectly to an under stomach member 360 having a greater width/length (or area) than the strap 330, such as a pad 360p that can reside under a patient (FIGS. 16B, 18C). The term "pad" is used broadly and refers to any single layer of material or multiple layers of material with or without cushioning properties.

Figure 15:
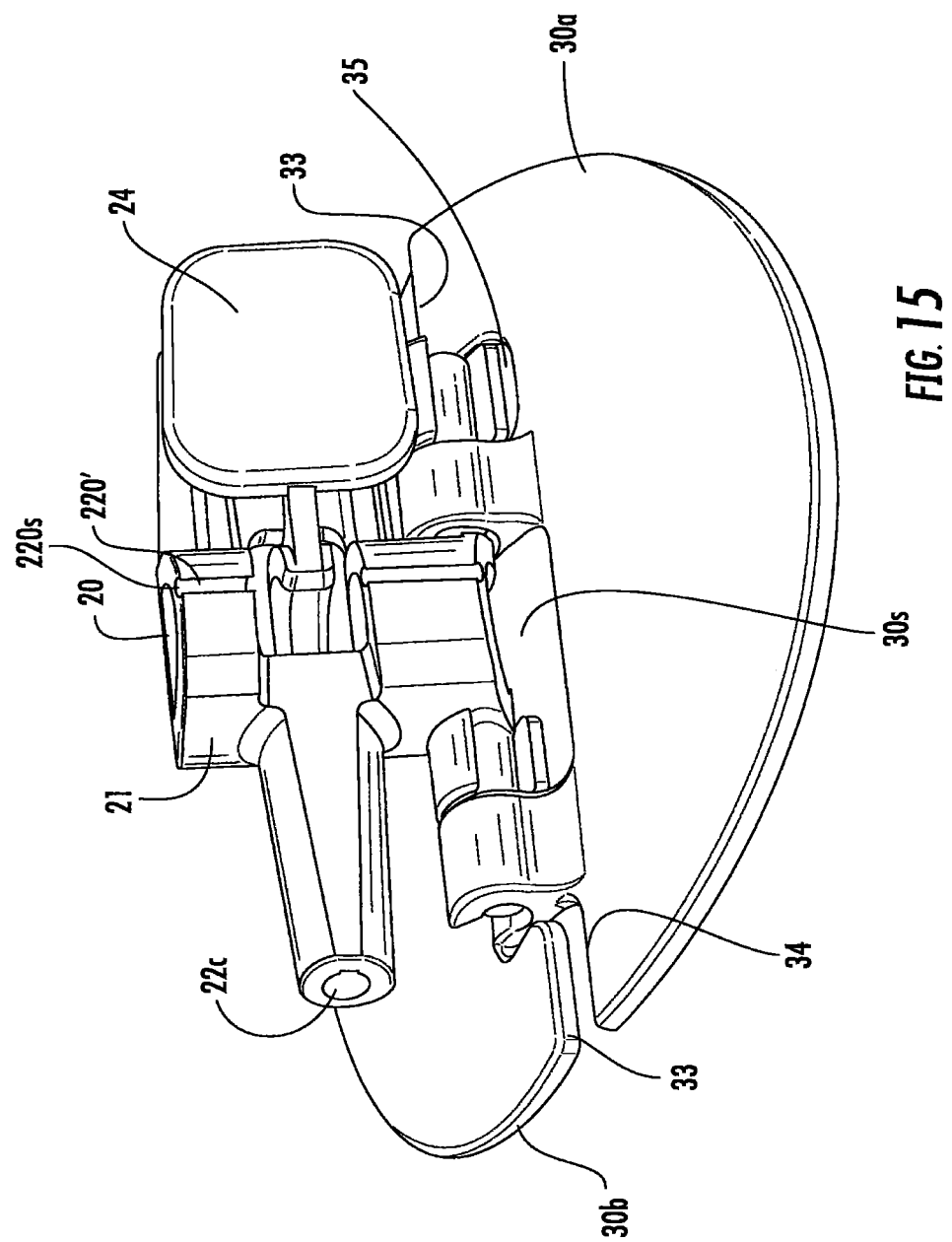
FIG. 15 is a side, perspective view of a column support member with an external k-wire or guide pin channel according to embodiments of the present invention.

The k-wires 120 (which can optionally also be interchangeably referred to as "pins") can extend through respective longitudinally extending channels 220 in the column support/tube 20. The K-wires 120 may be threaded K-wires. The channels 220 can be in the upwardly extending wall 21 of the column support or may be formed on an outer or inner perimeter to snugly receive a respective k-wire 120 (FIG. 15). The channels 220 can have a diameter that is between about 0.75-2 mm, more typically about 1.0-1.75 mm. In some embodiments, where the k-wire or pin channels 220 are used, the external base 30 is optional. The strap 330 (FIG. 12) is also optional.

Where used, the k-wires 120 can have a sharp end 120t and a blunt end 120b configured to allow a user to force down against the blunt end 120b to "tap" against it to position the sharp end 120t in a target spinal facet joint, typically in bone or hard tissue for anchoring. The k-wires 120 can have a length that is the same or slightly shorter or longer than the portal tube 40, typically about 10%-30% shorter so that they reside below an upper end of the portal tube 40, in position in a patient, as shown in FIG. 12, for example. The k-wires 120 can reside spaced apart about the perimeter of the upwardly extending wall 21 the tubular member 20, typically diametrically opposed from each other, at least where only two such k-wires are used.

The k-wires 120 can include an insulating material 120m (FIG. 14A) as a coating, sheath or substrate material that can be an electric and/or thermal insulator, such as a polymer, ceramic or other non-electrically conductive and/or reduced or non-heat conductive material. The entire length of the k-wires 120 can include the insulating material or a defined sub-segment or sub-segments may include this material. That is, for example, the tip or most distal segment of between about 1-3 mm may be devoid of the insulating material 120m and may be a surgical grade metallic material. The insulating material 120m may be only on an external portion (at or above the skin) or along sub-lengths of both internal and external portions, for example.

Figure 13B:
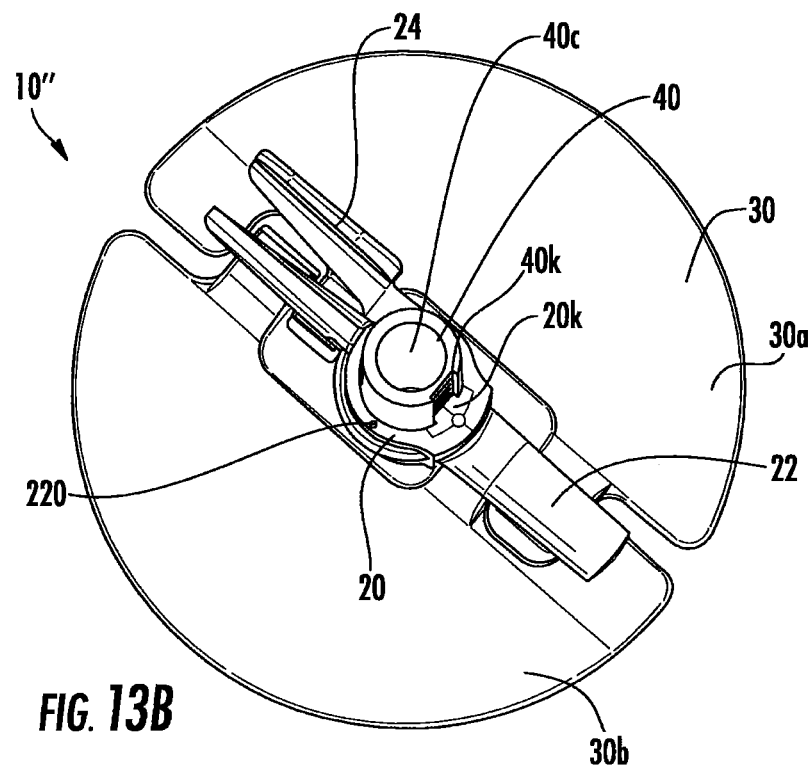
FIG. 13B is a top, side perspective view of the tool shown in FIG. 12 with an alternate alignment key feature according to embodiments of the present invention.
Figure 13A:
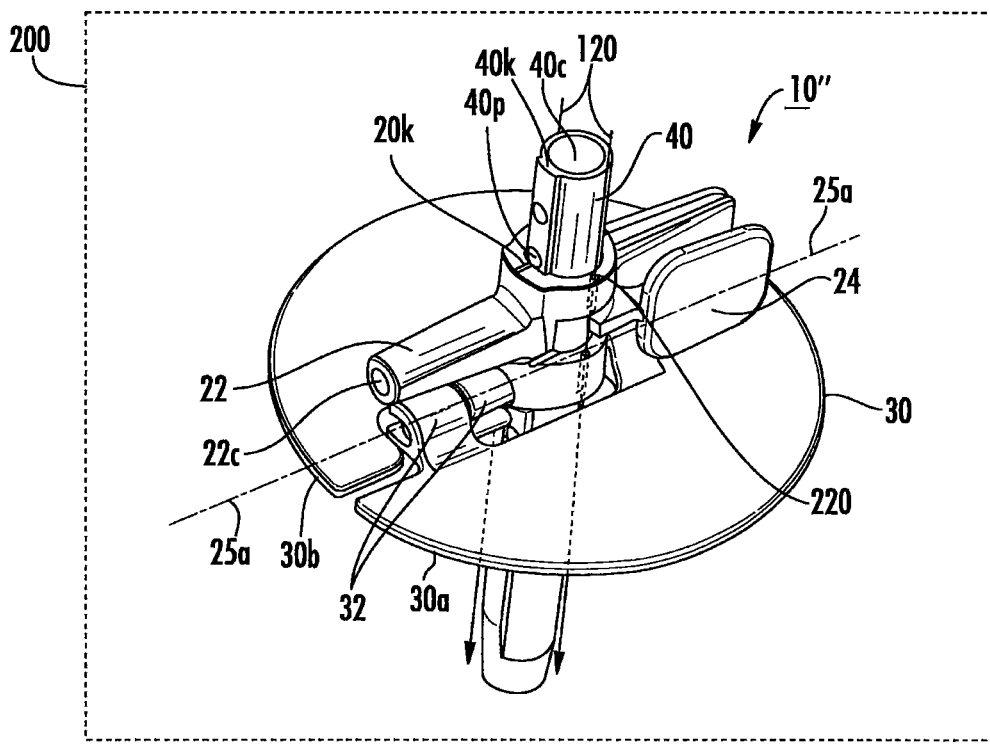
FIG. 13A is a top perspective view of the tool shown in FIG. 12.
Figure 13C:
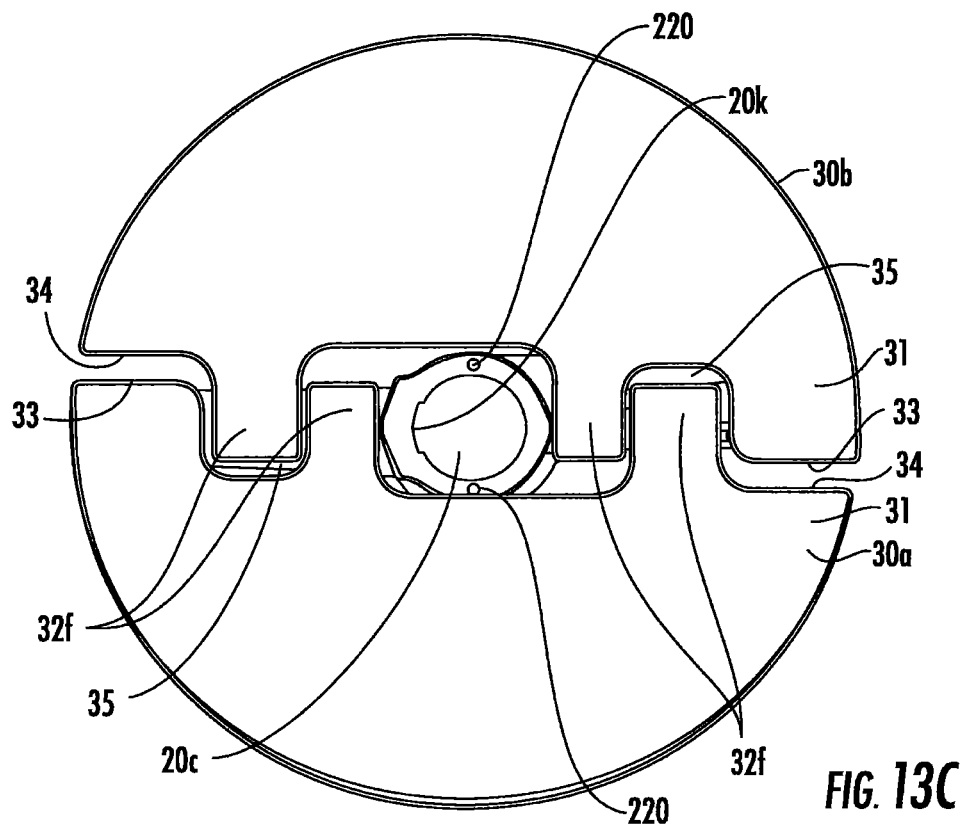
FIG. 13C is a bottom view of a stabilizer and column support member according to embodiments of the present invention.
Figure 13D:
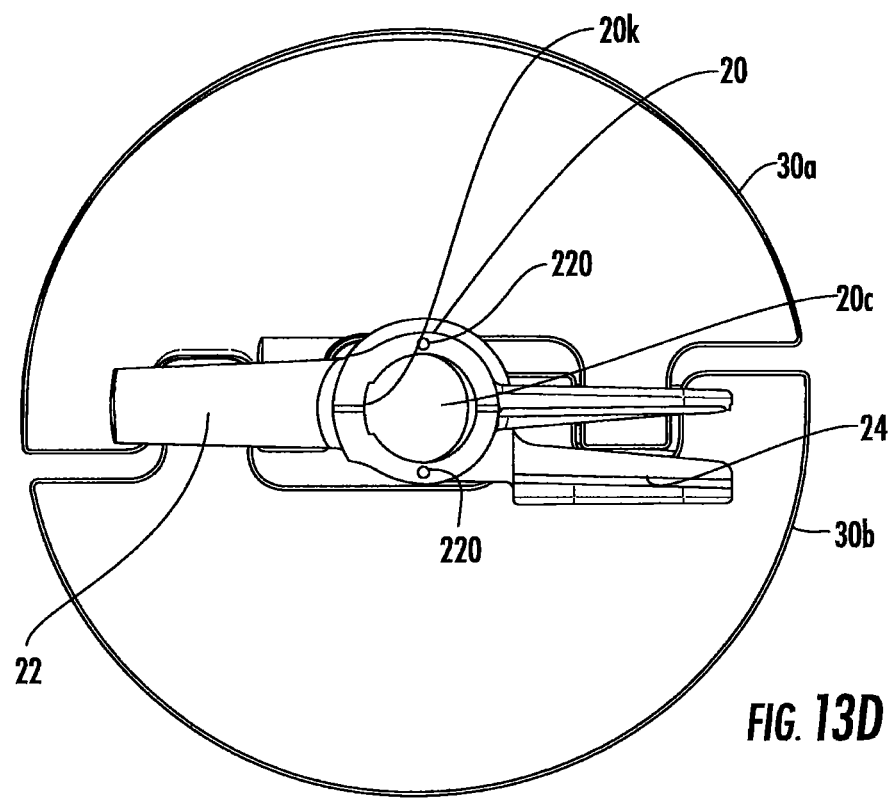
FIG. 13D is a top view of the stabilizer and column support member shown in FIG. 13A.
Figure 13E:
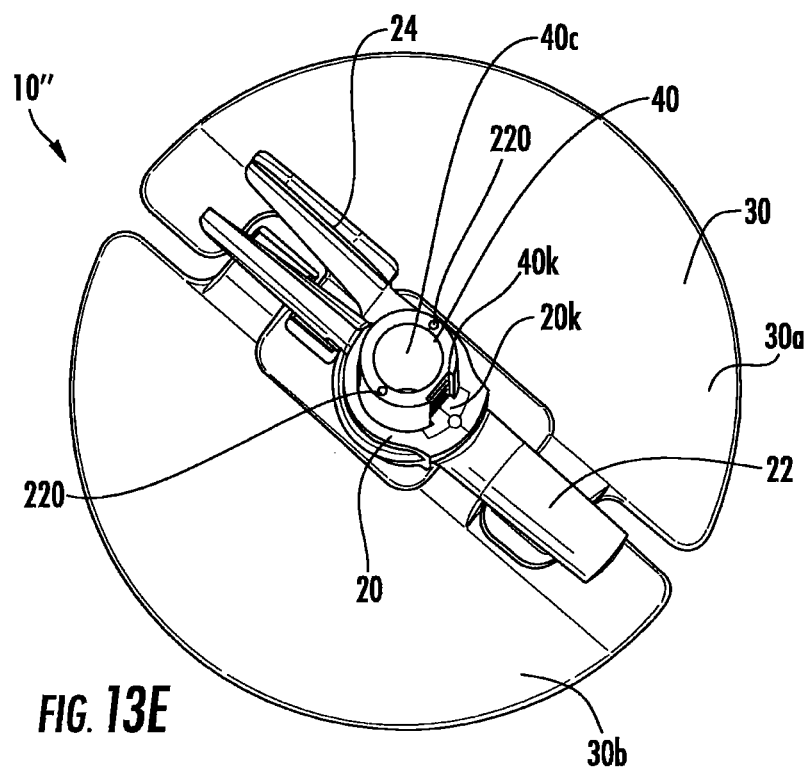
FIG. 13E is a top perspective view of the device shown in FIG. 13B but illustrating that the k-wire channels can reside in the guide cannula according to embodiments of the present invention.

FIGS. 13A-13D show the stabilizer tool 10" with the column support/tubular member 20 with the outwardly extending vacuum arm 22 and with longitudinally extending channels 220. FIGS. 13A-13D show the channels 220 in or on the wall of the tubular member 21. FIG. 13E shows the channels 220 in the wall of the guide cannula 40 with the ports 40p. The channels 220 can extend in both the tubular support member 20 and the guide cannula 40 in some particular embodiments.

Figure 14B:
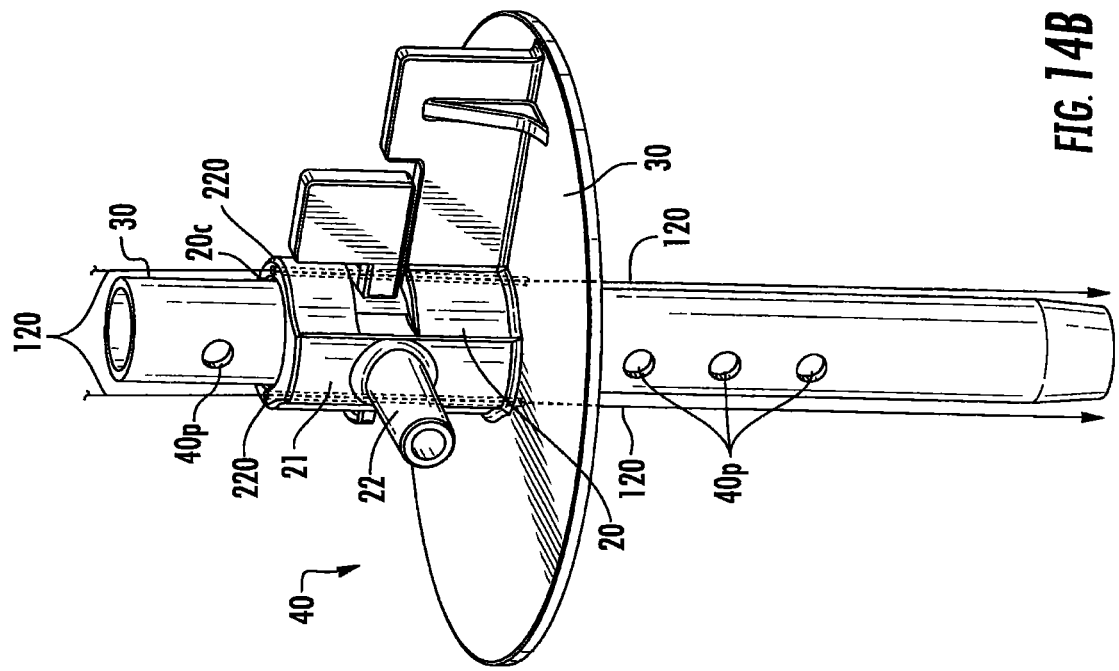
FIG. 14B is a side perspective view of the tool shown in FIG. 14A.
Figure 14A:
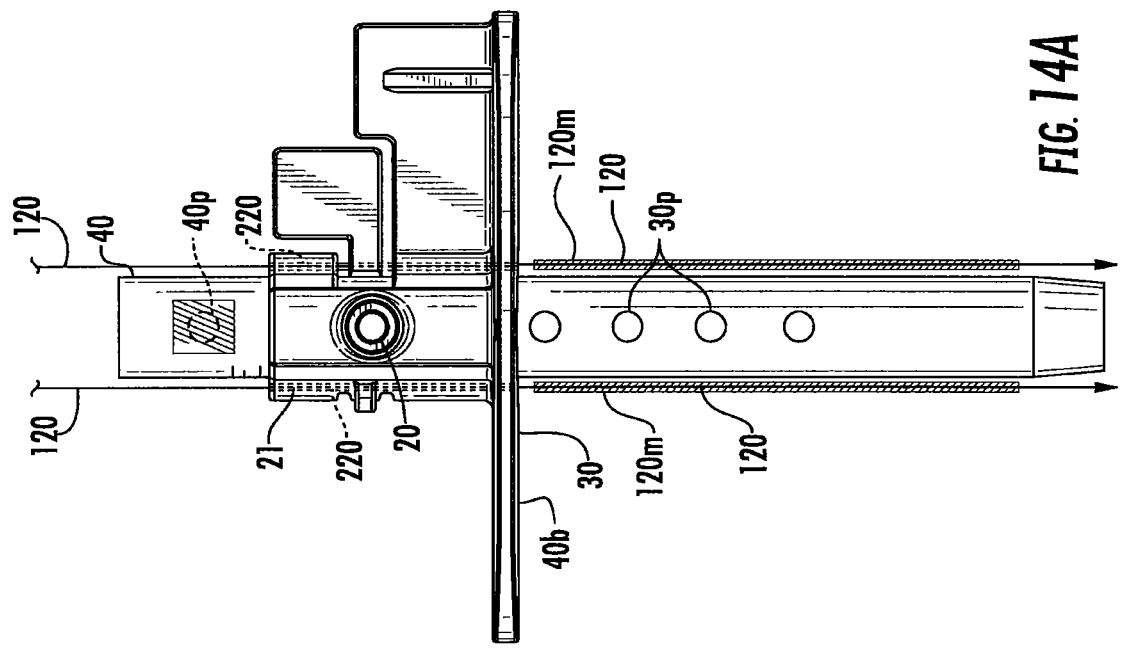
FIG. 14A is a side view of another embodiment of a surgical tool with a guide cannula and column support member according to embodiments of the present invention.

FIGS. 14A and 14B illustrate another embodiment of the surgical stabilizer tool with the guide cannula 40 and column support member 20 with the longitudinally extending channels 220 for the k-wires 120 according to embodiments of the present invention. In this embodiment, the external base 30 is not hinged and can be a unitary monolithic member.

FIG. 15 is a side, perspective view of a column support member 20 with the k-wire or guide pin channels 220' formed on an external or internal surface of the upwardly extending wall 21 (shown on the external surface) with a partially open longitudinally extending outer segment 220s configured to allow a respective k-wire to be "press-fit" into the channel 220 instead of threaded through an enclosed channel in the wall 21. according to embodiments of the present invention.

Figure 16A:
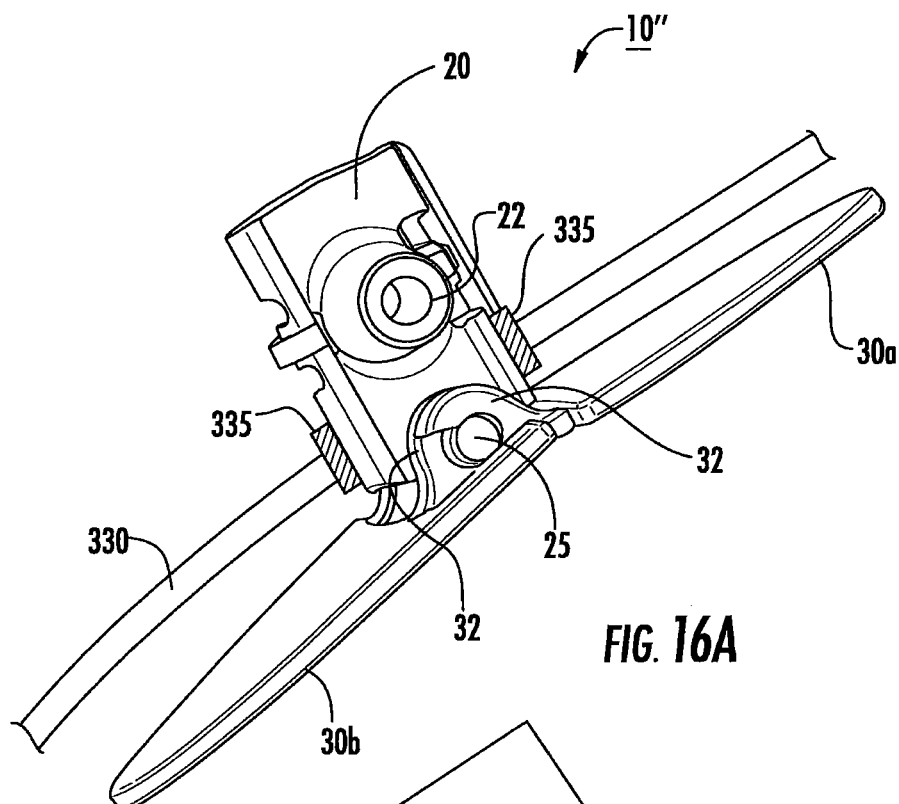
FIG. 16A is a side, perspective view of another embodiment of a surgical tool with a column support member according to embodiments of the present invention.
Figure 16B:
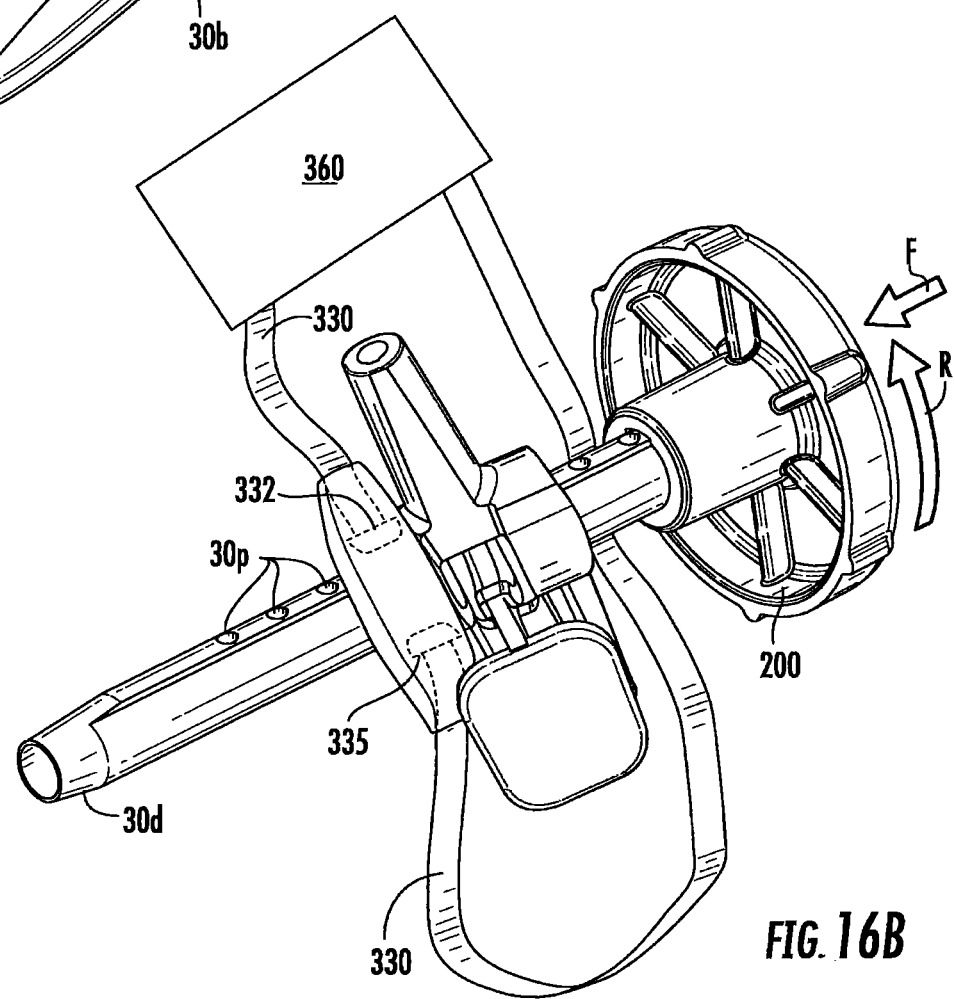
FIG. 16B is a side perspective view of yet another embodiments of the present invention.

FIG. 16A illustrates another embodiment of a surgical stabilizer tool 10" with a column support member 20 cooperating with a strap 330 according to embodiments of the present invention. Instead of the ring 330r shown in FIG. 12, for example, the strap 330 can attach to diametrically opposed anchor segments 335 on the tubular member 20. FIG. 16B shows the strap 330 attached to an exemplary pad 360p and also illustrates that the base 30 is optional. FIG. 16B also illustrates a hand grip 200 that can allow a user to manually rotate and push against the guide cannula 40. The guide cannula 40 may optionally have a recessed or projecting key segment 40k.

Figure 17:
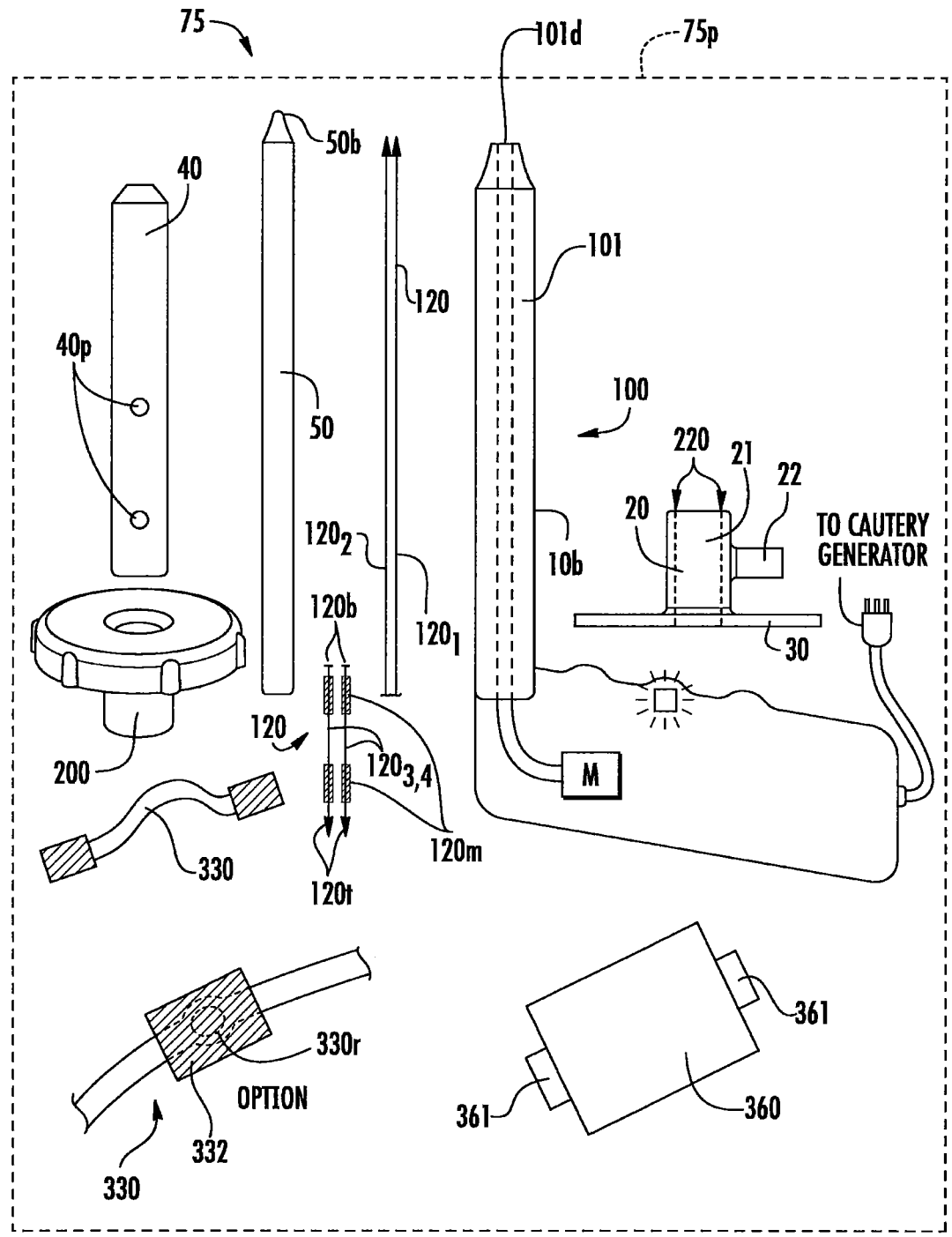
FIG. 17 is a schematic illustration of a kit and/or set of surgical tools for a spinal facet surgery according to embodiments of the present invention.

FIG. 17 illustrates an example of a spinal facet debridement surgical tool kit 75. As shown, the kit 75 can include a package 75p with sterile components that facilitate the surgery. The kit 75 can include a debrider tool 100 (which can be the entire therapy delivery tool 101 or a consumable, single use disposable or multi-use barrel), optionally a plurality of guide pins or k-wires 120. The k-wires or guide pins 120 can be provided in a common size or different sizes, typically with a diameter that is between about 0.75-1.5 mm, more typically about 1.0-1.4 mm.

As shown, the kit 75 can include k-wires 120 with a thermally and/or electrically insulating material 120m.

The kit 120 may include or more long k-wires $120_1$, $120_2$ and a one or more (typically a plurality) of shorter k-wires $120_3$, $120_4$, but one or more than two of each length can be provided, or the pins/k-wires 120 can also be provided separately outside the kit. The shorter k-wires/pins 120 can be 20-50% shorter than the longer k-wires/pins 120 and may include the insulating material 120m.

The kit 75 may also include a strap 330 which may have at least one sterile-cover 332 that may optionally be a peel-away sterile cover. The sterile cover 332 can insure that the segment of the strap 330 that will be over the patient surgical sterile space be kept in a sterile condition prior to use/placement. The strap 330 can have different lengths/shapes. For example, as shown with respect to two exemplary strap alternatives in the kit 75, the strap 330 can have ends that attach to the tubular member 20 or may have a ring 330r. The kit 75 may also include a pad 360 with attachment features/members 361 (VELCRO® hook and loop fasteners, hooks, buckles and the like) for securing to ends of the strap 330 to form a closed perimeter configuration about the tubular member 21.

The kit 75 can also include a dilation tube 50 with a tapered end 50b and at least one guide cannula 40 (or working tube) with vacuum ports 40p, and the column support 21 with a vacuum port 22. The kit 75 may also include the hand grip member 200. While shown as kits with all the noted components for facilitating ease of surgical preparation, the components may be provided as separate units or sub-sets. The k-wires wires $120_3$, $120_4$ can be sized and configured to attach to and/or extend through channels 220, 220' in or on the support column 20 while one or more other ones can be configured to extend through the dilation tube 50 for proper positioning of the guide cannula 40, then removed prior to initiating the therapy, typically with, after or prior to removal of the dilation tube 50 and after the k-wires 120 with the insulating material 120m are attached to the tubular support member 20 and/or strap 330 is attached to the patient/tubular support member 20 and/or guide cannula 40.

The guide cannula 40 can be provided pre-attached to the dilation tube 50 or hand grip 200, or may be provided as a separate unassembled component. For bilateral and/or multi-level procedures, more than one guide cannula 40 and, where used, more than one stabilizer 10, 10', 10" may be included, and if so, may be labeled for right and left sides and/or for indicating spinal treatment levels. See, e.g., co-pending U.S. patent application Ser. Nos. 14/257,490 and 14/810,683, the contents of which are hereby incorporated by reference as if recited in full herein, for examples of suitable tools for spinal facet treatments.

Figure 18A:
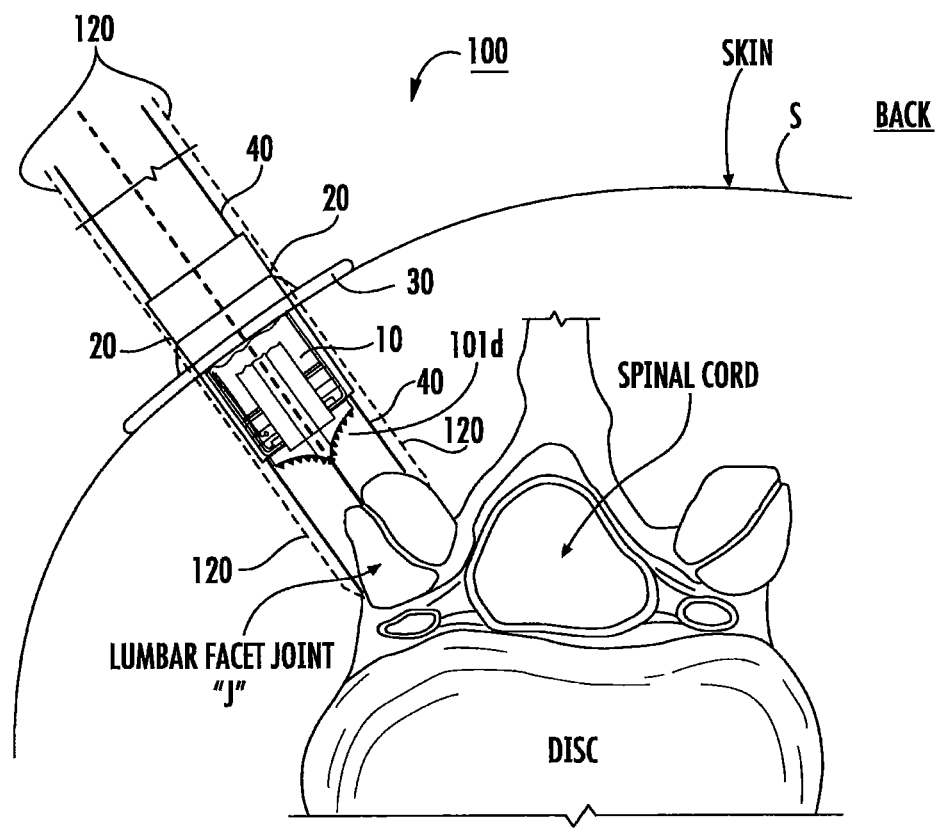
FIGS. 18A-18C are schematic illustrations of different configurations of surgical tools for spinal facet joint therapy according to embodiments of the present invention.
Figure 18B:
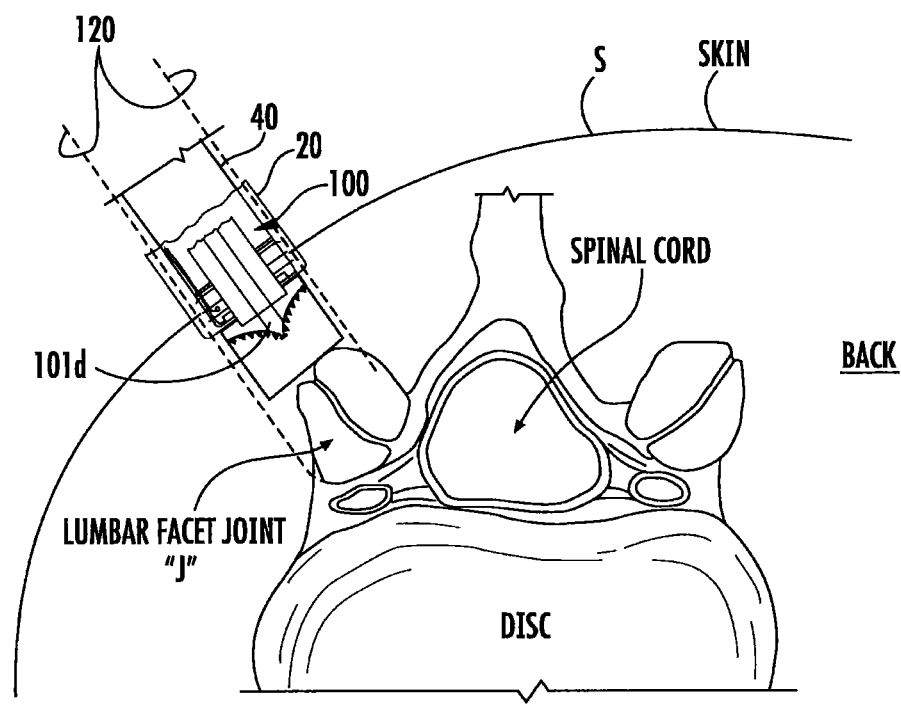
Figure 18C:
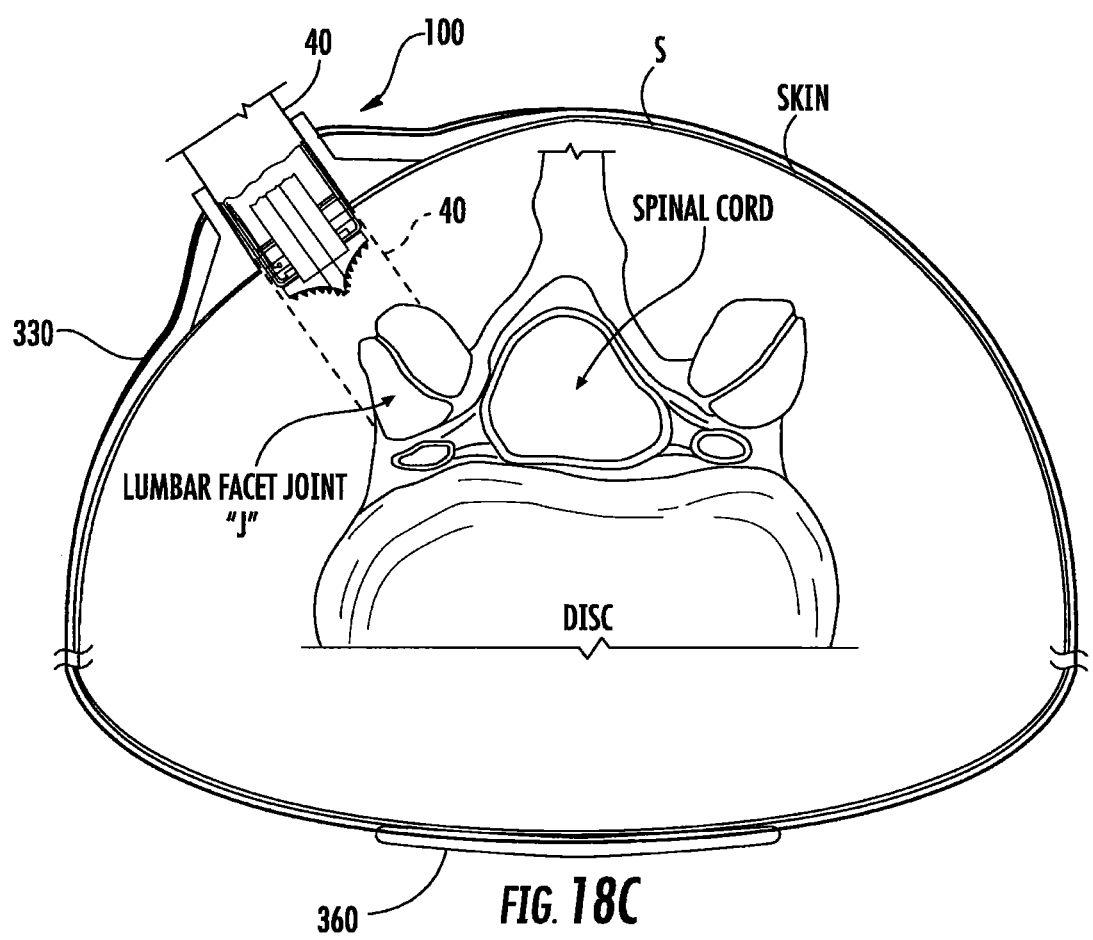

FIGS. 18A-18C are schematic illustrations of different configurations of surgical tools for spinal facet joint therapy according to embodiments of the present invention. FIG. 18A shows the stabilizer 10" with the support member 20 having channels 220 holding k-wires 120 which extend to the facet joint J. FIG. 18B illustrates the tool 10" without the use of an external base 30. FIG. 18C illustrates the tool 10" with the strap 330 extending under the stomach of a patient optionally attached to a pad 360p. The strap(s) 330 connect to the portal tube 40 and/or column support 20, anchored by patient weight.

While the devices have been described with respect to spinal facet surgical treatments, it is contemplated that the stabilizer 10, 10', 10" may be suitable for use with other surgical tools and surgical procedures.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described That which is claimed:

1. A surgical tool comprising:
an upwardly extending tubular support member having a longitudinally extending open channel, the tubular support member comprising a wall surrounding the open channel; and
a base pivotably and directly attached to the tubular support member with a pivot axis that extends above a bottom surface of the base and across a bottom portion of the tubular support member to allow the tubular support member to pivot back and forth over the bottom surface of the base,
wherein the base comprises first and second base members adapted to concurrently press against skin of a patient, one attached to each side of the tubular support member, each configured to move independent of the other.

2. The surgical tool of claim 1, wherein the tubular support member terminates proximate the bottom surface of the base, wherein the pivot axis extends through an axially extending centerline of first and second laterally extending and spaced apart attachment members held by one of the tubular support member or base that cooperate with hinge members held by the other of the tubular support member or base to allow the tubular support member to pivot above the bottom surface of the base as the laterally extending attachment members rotate in the hinge members.

3. The surgical tool of claim 1, wherein the tubular support member comprises spaced apart first and second laterally outwardly extending base attachment members that have a fixed orientation relative to the tubular support member and define the pivot axis, and wherein the base comprises a plurality of hinge members, at least one that engages the first base attachment member and at least one that engages the second base attachment member.

4. The surgical tool of claim 3, wherein the laterally extending base attachment members are cylindrical, and wherein the first and second laterally extending base attachment members are in a fixed orientation that is orthogonal to an axially extending direction of the wall of the tubular support member and reside on the bottom portion of the tubular support member.

5. The surgical tool of claim 1, wherein the tubular support member resides entirely above the base, wherein the tubular support member further comprises first and second laterally outwardly extending base attachment members that reside above the bottom surface of the base that define the pivot axis, wherein the base comprises a plurality of hinge members, at least one that engages the first base attachment member and at least one that engages the second base attachment member, wherein the tubular support member further comprises laterally outwardly extending finger grips and a laterally extending fluid channel on an opposing side thereof, and wherein the finger grips and the fluid channel reside above the hinge members.

6. The surgical tool of claim 1, wherein the first and second base members are substantially semi-circular and are held by the tubular support member to define a circular outer perimeter of the base.

7. The surgical tool of claim 1, wherein the bottom surface of the base is curved in a direction facing away from the tubular support member.

8. The surgical tool of claim 1, wherein the bottom surface of the base has a radius of curvature measured from a virtual center point that in a use orientation is under the tubular support member, that is between about 4 inches to about 12 inches.

9. A surgical tool comprising:
an upwardly extending tubular support member having a longitudinally extending open channel, the tubular support member comprising a wall surrounding the open channel; and
a base pivotably and directly attached to the tubular support member with a pivot axis that extends above a bottom surface of the base and across a bottom portion of the tubular support member to allow the tubular support member to pivot back and forth over the bottom surface of the base,
wherein the base is a unitary member with upwardly extending hinge members that engage laterally outwardly extending arms extending off the wall of the tubular support member, wherein the tubular support member resides entirely above the bottom surface of the base and is externally visible, and wherein the bottom surface is sized and configured to reside against skin of a patient and has an outer perimeter with a width and/or length that is between about 2-6 inches.

10. A surgical tool comprising:
an upwardly extending tubular support member having a longitudinally extending open channel, the tubular support member comprising a wall surrounding the open channel; and
a base pivotably and directly attached to the tubular support member with a pivot axis that extends above a bottom surface of the base and across a bottom portion of the tubular support member to allow the tubular support member to pivot back and forth over the bottom surface of the base,
wherein the tubular support member comprises spaced apart first and second laterally outwardly extending base attachment members that have a fixed orientation relative to the tubular support member and define the pivot axis, and wherein the base comprises a plurality of hinge members, at least one that engages the first base attachment member and at least one that engages the second base attachment member,
wherein the tubular support member comprises at least one elongate radially outwardly extending fluid channel in fluid communication with the longitudinally extending open channel, wherein the tubular support member and the base pivot about only a single pivot axis as the pivot axis, wherein the single pivot axis axially extends through the first and second laterally outwardly extending base attachment members and across the tubular support member, and wherein the at least one elongate radially outwardly extending fluid channel resides above and parallel to the first and second laterally outwardly extending base attachment members.

11. A surgical tool comprising:
an upwardly extending tubular support member having a longitudinally extending open channel, the tubular support member comprising a wall surrounding the open channel;
a base pivotably and directly attached to the tubular support member with a pivot axis that extends above a bottom surface of the base and across a bottom portion of the tubular support member to allow the tubular support member to pivot back and forth over the bottom surface of the base; and a plurality of circumferentially spaced apart k-wires held by the tubular support member wherein the wall of the tubular support member comprises circumferentially spaced apart longitudinally extending channels that each receive a respective k-wire.

12. A surgical tool comprising:

an upwardly extending tubular support member having a longitudinally extending open channel, the tubular support member comprising a wall surrounding the open channel; and a base pivotably attached to the tubular support member with a pivot axis that extends above a bottom surface of the base and across a bottom portion of the tubular support member to allow the tubular support member to pivot back and forth over the bottom surface of the base, wherein the tubular support member comprises first and second laterally extending attachment arms extending outwardly off the wall of the tubular support member in a fixed orientation relative to the tubular support member that define the pivot axis, wherein the base comprises first and second base members adapted to contact skin of a patient, each having upwardly extending first and second spaced apart hinge members, wherein the first hinge member of the first base member and the first hinge member of the second base member are attached to the first attachment arm and define a first cooperating pair of adjacent hinge members and the second hinge member of the first base member and the second hinge member of the second base member are attached to the second attachment arm and define a second cooperating pair of adjacent hinge members, and wherein the first and second base members can move up and down independent of the other and the tubular support member can pivot relative to the base about the pivot axis.

13. A surgical tool comprising:

an upwardly extending tubular support member having a longitudinally extending open channel, the tubular support member comprising a wall surrounding the open channel; and a base pivotably and directly attached to the tubular support member with a pivot axis that extends above a bottom surface of the base and across a bottom portion of the tubular support member to allow the tubular support member to pivot back and forth over the bottom surface of the base, in combination with a guide cannula, wherein the guide cannula is sized and configured to be held in the longitudinally extending open channel of the tubular support member, wherein the tubular support member comprises at least one elongate laterally outwardly extending fluid channel in fluid communication with the longitudinally extending open channel thereof, wherein the guide cannula has a wall that surrounds an open longitudinally extending channel, wherein the wall of the guide cannula comprises at least one open aperture in fluid communication with the fluid channel of the tubular support member, wherein the tubular support member and the base pivot about only a single pivot axis as the pivot axis, wherein the single pivot axis axially extends through first and second laterally outwardly extending base attachment members and across the tubular support member, and wherein the at least one radially outwardly extending fluid channel resides above and parallel to the first and second laterally outwardly extending base attachment members.

14. The surgical tool of claim 13, in further combination with a debridement surgical tool that extends through the open channel of the guide cannula while the guide cannula is held by the tubular support member.

15. A surgical tool comprising:

an upwardly extending tubular support member having a longitudinally extending open channel, the tubular support member comprising a wall surrounding the open channel; and a base pivotably and directly attached to the tubular support member with a pivot axis that extends above a bottom surface of the base and across a bottom portion of the tubular support member to allow the tubular support member to pivot back and forth over the bottom surface of the base, wherein the base has an upper surface that is planar and defines first and second laterally spaced apart hinge members that project upward above the planar upper surface and that slidably receive arms extending out from the tubular support member, wherein the tubular support member resides entirely above the bottom surface of the base, wherein the surgical tool comprises at least one strap coupled to the tubular member, and wherein the strap has a length sufficient to define a closed configuration extending about a torso of a patient and/or attaches to opposing sides of an anchor pad under a patient to define a closed perimeter configuration.

16. A surgical tool comprising:

an upwardly extending tubular support member having a longitudinally extending open channel, the tubular support member comprising a wall surrounding the open channel; and a base pivotably and directly attached to the tubular support member with a pivot axis that extends above a bottom surface of the base and across a bottom portion of the tubular support member to allow the tubular support member to pivot back and forth over the bottom surface of the base, wherein the pivot axis extends through an axially extending centerline of first and second laterally spaced apart and laterally extending attachment arms held by one of the tubular support member or base that cooperate with hinge members held by the other of the tubular support member or base to allow the tubular support member to pivot above the bottom surface of the base as the first and second attachment arms rotate in the hinge members, wherein the first and second attachment arms are cylindrical and extend orthogonally outward from the wall of the tubular support member in a fixed orientation relative to the tubular support member, and wherein the hinge members are provided as a first pair of hinge members that define a laterally extending cylindrical channel that slidably engages the first attachment arm and a second pair of hinge members that define a laterally extending cylindrical channel that slidably engages the second attachment arm.

17. The surgical tool of claim 16, wherein the hinge members have an arcuate upper segment and merge into a flat bottom segment under the cylindrical channel, wherein the first pair of hinge members have an open outer perimeter segment that face opposing directions to thereby slidably receive the first attachment arm, and wherein the second pair of hinge members define an open outer perimeter segment that face opposing directions to thereby slidably receive the second attachment arm.

18. Surgical tools for spinal facet therapy comprising:
a debrider tool with an elongate rotatable shaft having a distal end with a denuding and cauterization head, and a motor in communication with the shaft to drive the rotatable denuding and cauterization head;
a guide cannula that holds the shaft of the debrider tool during a therapy;
a tubular support member comprising a longitudinally extending channel sized to allow the guide cannula to extend therethrough, the tubular support member comprising a wall enclosing the longitudinally extending channel, and an arm with a vacuum port extending laterally outward from the wall; and
a base pivotably attached to the tubular support member having a pivot axis that extends above a bottom surface of the base across a bottom portion of the tubular support member, wherein the base comprises first and second base members, wherein, in use, the base is adapted to rest against skin of a patient, wherein the tubular support member terminates adjacent the bottom surface of the base and comprises an open longitudinally extending channel that holds the guide cannula with the shaft of the debrider tool extending through the guide cannula to allow the tubular support member, guide cannula and rotatable shaft to pivot back and forth about the pivot axis over the bottom surface of the base while the shaft of the tool rotates during a therapy,
wherein the arm comprises at least one fluid channel that is in fluid communication with an open longitudinally extending channel of the guide cannula, wherein the tubular support member further comprises first and second laterally extending base attachment members that have a fixed orientation relative to the tubular support member and are orthogonal to an axially extending direction of the tubular support member, wherein the first and second laterally extending base attachment members reside on the bottom portion of the tubular support member, below the arm, and wherein the base comprises hinge members provided as a first pair of hinge members that define a first laterally extending cylindrical channel that slidably engages the first base attachment member and a second pair of hinge members that define a second laterally extending cylindrical channel that slidably engages the second base attachment member.

19. The surgical tools of claim 18, wherein the first and second base members are adapted to concurrently rest against skin of a patient, one attached to each side of the tubular support member, each configured to move independent of the other.

20. The surgical tools of claim 19, wherein the tubular support member resides entirely above the bottom surface of the base, and wherein the tubular support member and the base pivot about only a single pivot axis as the pivot axis.

21. The surgical tools of claim 18, wherein, in a use orientation, the base is curved in a direction facing away from the tubular support member toward a target spinal facet joint.

22. The surgical tools of claim 18, wherein the bottom surface of the base has a radius of curvature measured from a virtual center point that in a use orientation is under the tubular support member that is between about 4 inches to about 12 inches, and wherein the tubular support member resides entirely above the bottom surface of the base and is externally visible.

23. The surgical tools of claim 18, wherein the tubular support member comprises k-wires, and wherein the tubular support member comprises longitudinally extending channels that receive a respective k-wire.

24. The surgical tools of claim 18, wherein the tubular support member is coupled to a strap, and wherein the strap has a length sufficient to define a closed configuration extending about a torso of a patient or attaches to opposing sides of an anchor pad under a patient to define a closed perimeter configuration.

25. A set of surgical tools for spinal facet therapy comprising:
a surgical therapy tool with an elongate rotatable shaft having a distal end with a rotatable cauterization head, and a motor in communication with the shaft to drive the rotatable cauterization head;
a guide cannula that holds the shaft of the surgical therapy tool during a therapy; and
a tubular support member comprising a longitudinally extending channel sized to allow the guide cannula to extend therethrough, the tubular support member comprising an outwardly extending arm with a vacuum port; and
a base pivotably attached to the tubular support member having a pivot axis that extends above a bottom surface of the base across a bottom portion of the tubular support member, wherein, in use, the base is adapted to rest against skin of a patient, wherein the base comprises:
first and second base members that have a planar bottom surface and that are both adapted to concurrently rest against skin of a patient, one attached to each side of the tubular support member, each configured to move independent of the other; and
an open longitudinally extending channel that holds the guide cannula with the shaft of the surgical therapy tool extending through the guide cannula to allow the tubular support member, guide cannula and rotatable shaft to pivot back and forth about the pivot axis over the bottom surface of the base while the shaft of the surgical therapy tool rotates during a therapy,
wherein the pivot axis extends through an axially extending centerline of first and second attachment arms that are laterally spaced apart and laterally extending and held by the tubular support member, wherein the first and second attachment arms cooperate with hinge members held by the base to allow the tubular support member to pivot above the bottom surface of the base as the first and second attachment arms rotate in the hinge members, wherein the first and second attachment arms are cylindrical and extend orthogonally outward from an outer wall of the tubular support member in a fixed orientation relative to the tubular support member, and wherein the hinge members are provided as a first pair of hinge members that define a laterally extending cylindrical channel that slidably engages the first attachment arm and a second pair of hinge members that define a laterally extending cylindrical channel that slidably engages the second attachment arm.

26. The surgical tool of claim 25, wherein the first pair of hinge members have an open outer perimeter segment that face opposing directions to thereby slidably receive the first attachment arm, and wherein the second pair of hinge members have an open outer perimeter segment that face opposing directions to thereby slidably receive the second attachment arm.

* * * * *

UNITED STATES PATENT AND TRADEMARK OFFICE
CERTIFICATE OF CORRECTION

PATENT NO. : 10,595,919 B2
APPLICATION NO. : 15/527920
DATED : March 24, 2020
INVENTOR(S) : Haufe et al.

It is certified that error appears in the above-identified patent and that said Letters Patent is hereby corrected as shown below:

In the Specification

Column 9, Line 25: DELETE "25*e*" INSERT -- 25*c* --

Column 18, Line 27: DELETE "101*bf*" INSERT -- 10 lb$_f$ --

Signed and Sealed this
Twenty-eighth Day of July, 2020

Andrei Iancu
*Director of the United States Patent and Trademark Office*